United States Patent
Hartmann et al.

(10) Patent No.: US 9,579,161 B2
(45) Date of Patent: Feb. 28, 2017

(54) METHOD AND APPARATUS FOR TRACKING A PATIENT

(75) Inventors: Steven L. Hartmann, Superior, CO (US); Laurent Verard, Superior, CO (US); James Kelley, Coon Rapids, MN (US); Kenneth Gardeski, Plymouth, MN (US); Kevin Thomas Wu, Lakewood, CO (US); Michael Neidert, Salthill (IE)

(73) Assignee: Medtronic Navigation, Inc., Louisville, CO (US)

( * ) Notice: Subject to any disclaimer, the term of this patent is extended or adjusted under 35 U.S.C. 154(b) by 2397 days.

(21) Appl. No.: 12/115,907

(22) Filed: May 6, 2008

(65) Prior Publication Data
US 2009/0281417 A1    Nov. 12, 2009

(51) Int. Cl.
*A61B 34/20* (2016.01)

(52) U.S. Cl.
CPC ...... *A61B 34/20* (2016.02); *A61B 2034/2051* (2016.02); *A61B 2090/364* (2016.02)

(58) Field of Classification Search
CPC ........ A61B 19/5244; A61B 2019/5251; A61B 2019/5289
USPC ................................. 600/424, 426, 414, 417
See application file for complete search history.

(56) References Cited

U.S. PATENT DOCUMENTS

| | | | |
|---|---|---|---|
| 5,592,939 A | 1/1997 | Martinelli | |
| 5,913,820 A | 6/1999 | Bladen et al. | |
| 6,161,032 A * | 12/2000 | Acker | 600/424 |
| 6,381,485 B1 | 4/2002 | Hunter et al. | |
| 6,473,635 B1 | 10/2002 | Rasche | |
| 6,474,341 B1 | 11/2002 | Hunter et al. | |
| 7,239,732 B1 * | 7/2007 | Yamada | 382/132 |
| 2003/0191394 A1 * | 10/2003 | Simon | A61B 6/481 600/473 |
| 2004/0097806 A1 | 5/2004 | Hunter et al. | |
| 2004/0158146 A1 * | 8/2004 | Mate et al. | 600/427 |
| 2004/0215071 A1 * | 10/2004 | Frank et al. | 600/407 |
| 2005/0085714 A1 | 4/2005 | Foley et al. | |

(Continued)

FOREIGN PATENT DOCUMENTS

WO    WO-2006051523 A2    5/2006

OTHER PUBLICATIONS

International Search Report and Written Opinion mailed Nov. 17, 2009 for PCT/US2009/042955 claiming benefit of U.S. Appl. No. 12/115,907, filed May 6, 2008.

(Continued)

*Primary Examiner* — Katherine Fernandez
(74) *Attorney, Agent, or Firm* — Harness, Dickey

(57) ABSTRACT

A system for tracking a patient is provided. The system can include a first reference frame coupled to a first portion of an anatomical structure. The system can include a second reference frame, which can be coupled to a second portion of the anatomical structure. The system can also include a first tracking device coupled to the first reference frame and a second tracking device coupled to the second reference frame. The system can also include a tracking system that can track a position of the first tracking device and the second tracking device to ensure that the position of the first reference frame relative to the anatomical structure is substantially the same throughout a surgical procedure.

28 Claims, 17 Drawing Sheets

(56) References Cited

U.S. PATENT DOCUMENTS

2005/0085715 A1\* 4/2005 Dukesherer et al. ......... 600/424
2007/0106152 A1 5/2007 Kantrowitz et al.

OTHER PUBLICATIONS

Office action for corresponding European Application No. 09743544.0-1654 dated Apr. 14, 2016.

\* cited by examiner

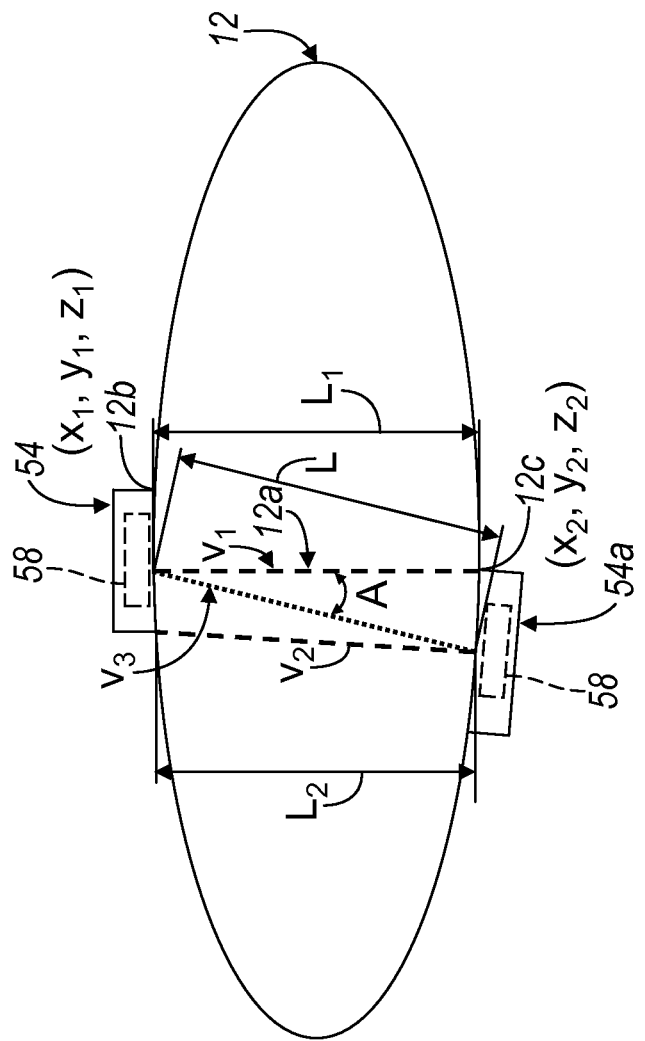

METHOD AND APPARATUS FOR TRACKING A PATIENT

FIELD

The present disclosure relates generally to navigated surgery, and more specifically, to systems and methods for tracking a patient.

BACKGROUND

The statements in this section merely provide background information related to the present disclosure and may not constitute prior art.

Image guided medical and surgical procedures utilize patient images (image data) obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in navigated medical procedures.

Generally, during a navigated procedure, images are acquired by a suitable imaging device for display on a workstation. The navigation system tracks the patient, instruments and other devices in the surgical field or patient space. These tracked devices are then displayed relative to the image data on the workstation in image space. In order to track the patient, instruments and other devices, the patient, instruments and other devices can be equipped with tracking devices.

Generally, tracking devices are coupled to an anatomical structure of the patient, and can provide the surgeon, via the tracking system, with an accurate depiction of the location of the patient in the patient space. In some instances, the tracking device coupled to the patient may move relative to the patient, such as in the case of an adhesively coupled or stick-on patient tracking device. In cases where the stick-on patient tracking device moves relative to the patient, it may be difficult to accurately determine the location of the patient in the patient space.

SUMMARY

A system for tracking a patient is provided. The system can include a first reference frame coupled to a first portion of an anatomical structure. The system can include a second reference frame, which can be coupled to a second portion of the anatomical structure. The system can also include a first tracking device coupled to the first reference frame and a second tracking device coupled to the second reference frame. The system can also include a tracking system that can track a position of the first tracking device and the second tracking device to ensure that the position of the first reference frame relative to the anatomical structure is substantially the same throughout a surgical procedure.

Further provided is a method for tracking a patient. The method can include coupling a first reference frame to a first portion of an anatomical structure adjacent to a surgical site. The first reference frame can include a first tracking device. The method can further include coupling a second reference frame to a second portion of the anatomical structure opposite the first reference frame. The second reference frame can include a second tracking device. The method can include tracking a position of the first tracking device of the first reference frame and the second tracking device of the second reference frame. The method can further include determining, based on the tracking of the first reference frame and the second reference frame, if the first reference frame has moved relative to the anatomical structure.

Also provided is a system for tracking a patient. The system can include a first reference frame coupled to a first portion of an anatomical structure of the patient. The system can also include a second reference frame coupled to a second portion of the anatomical structure opposite the first portion. The system can further include a first tracking device coupled to the first reference frame and a second tracking device coupled to the second reference frame. The system can include a tracking system that tracks a location of the first tracking device and the second tracking device. The system can also include a navigation system that determines the location of the first reference frame and the second reference frame based on the tracking of the first tracking device and the second tracking device. The system can further include a display that displays an image of the anatomical structure. The navigation system can determine if the image displayed is accurate based on a difference existing between the location of the first reference frame and the location of the second reference frame.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 2A is a simplified cross-sectional illustration of the patient of FIG. 1, taken along line 2-2 of FIG. 1, including a first reference frame and a second reference frame;

DETAILED DESCRIPTION

Figure 1:
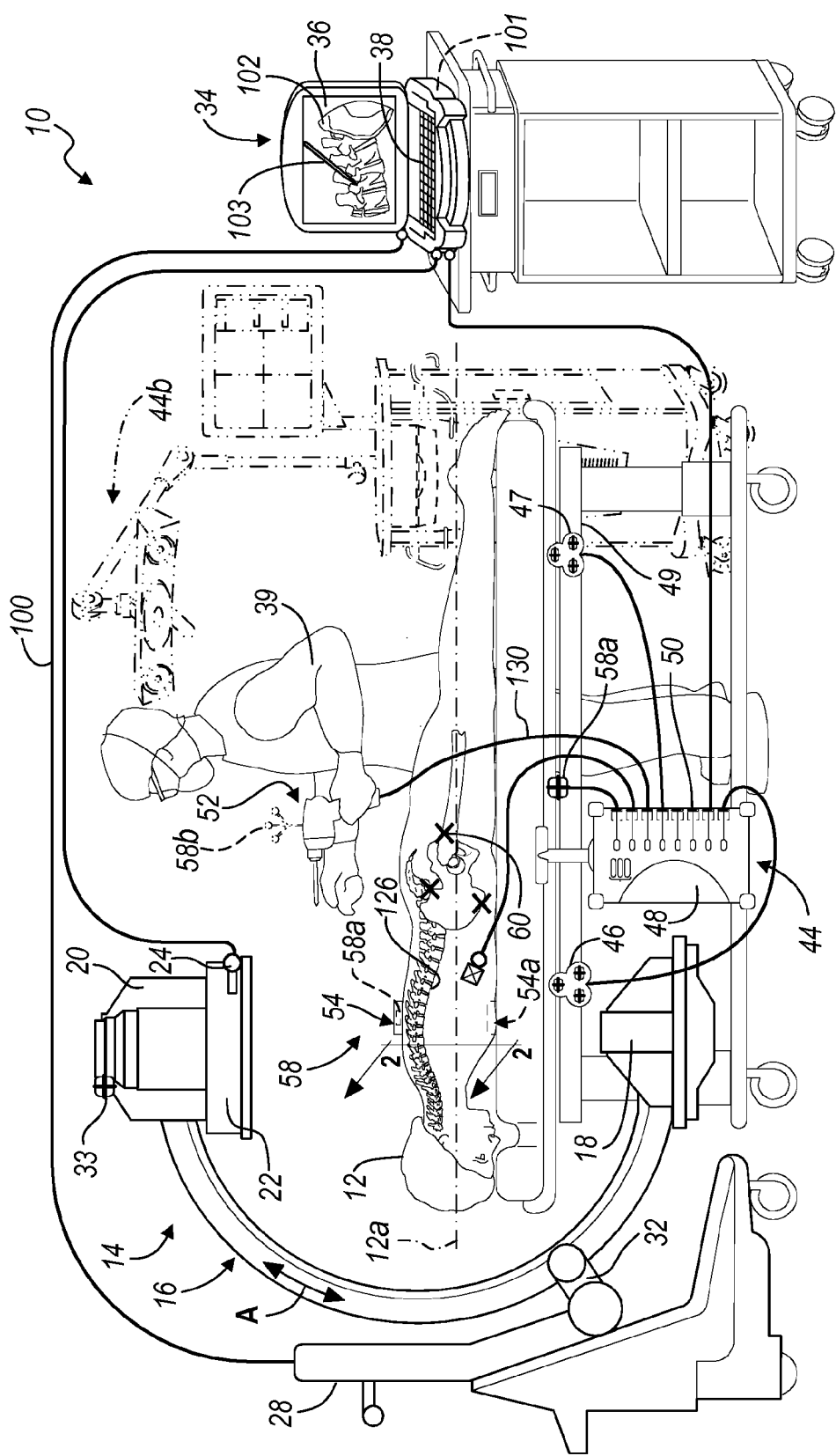
FIG. 1 is a diagram of a navigation system for performing a surgical procedure on a patient according to various embodiments of the present disclosure.

The following description is merely exemplary in nature and is not intended to limit the present disclosure, application, or uses. It should be understood that throughout the drawings, corresponding reference numerals indicate like or corresponding parts and features. As indicated above, the present teachings are directed toward providing a system and method for a dynamic reference frame tracker for use with a surgical procedure. It should be noted, however, that the present teachings could be applicable to any appropriate procedure in which it is desirable to determine a position of an object in which a tracking device coupled to the object may move relative to the object. Further, as used herein, the term module can refer to an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality. Therefore, it will be understood that the following discussions are not intended to limit the scope of the appended claims.

FIG. 1 is a diagram illustrating an overview of a navigation system 10 that can be used for various procedures. The navigation system 10 can be used to track the location of an implant, such as a spinal implant or orthopedic implant, relative to a patient 12. Also the navigation system 10 can track the position and orientation of various instruments. It should further be noted that the navigation system 10 may be used to navigate any type of instrument, implant, or delivery system, including: guide wires, arthroscopic systems, cardiac leads, orthopedic implants, spinal implants, deep-brain stimulator (DBS) probes, etc. Moreover, these instruments may be used to navigate or map any region of the body. The navigation system 10 and the various instruments may be used in any appropriate procedure, such as one that is generally minimally invasive, arthroscopic, percutaneous, stereotactic, or an open procedure.

The navigation system 10 may include an imaging device 14 that is used to acquire pre-, intra-, or post-operative or real-time image data of a patient 12. Alternatively, various imageless systems can be used or images from atlas models can be used to produce patient images, such as those disclosed in U.S. Patent Pub. No. 2005-0085714, filed Oct. 16, 2003, entitled "METHOD AND APPARATUS FOR SURGICAL NAVIGATION OF A MULTIPLE PIECE CONSTRUCT FOR IMPLANTATION," incorporated herein by reference. The imaging device 14 can be, for example, a fluoroscopic x-ray imaging device that may be configured as an O-Arm™ or a C-arm 16 having an x-ray source 18, an x-ray receiving section 20, an optional calibration and tracking target 22 and optional radiation sensors 24. It will be understood, however, that patient image data can also be acquired using other imaging devices, such as those discussed above and herein.

In operation, the imaging device 14 generates x-rays from the x-ray source 18 that propagate through the patient 12 and calibration and/or tracking target 22, into the x-ray receiving section 20. This allows real-time visualization of the patient 12 and radio-opaque instruments in the cone of the X-rays. In the example of FIG. 1, a longitudinal axis 12a of the patient 12 is substantially in line with a mechanical rotational axis 32 of the C-arm 16. This can enable the C-arm 16 to be rotated relative to the patient 12, allowing images of the patient 12 to be taken from multiple directions or about multiple planes. An example of a fluoroscopic C-arm X-ray device that may be used as the optional imaging device 14 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc. An exemplary O-Arm™ imaging device is available from Medtronic Navigation Littleton of Littleton, Mass.

When the x-ray source 18 generates the x-rays that propagate to the x-ray receiving section 20, the radiation sensors 24 can sense the presence of radiation, which is forwarded to an imaging device controller 28, to identify whether or not the imaging device 14 is actively imaging. This information can also be transmitted to a coil array controller 48, further discussed herein.

The imaging device controller 28 can capture the x-ray images received at the x-ray receiving section 20 and store the images for later use. Multiple two-dimensional images taken by the imaging device 14 may also be captured and assembled by the controller 28 to provide a larger view or image of a whole region of the patient 12, as opposed to being directed to only a portion of a region of the patient 12. For example, multiple image data of a leg of the patient 12 may be appended together to provide a full view or complete set of image data of the leg that can be later used to follow contrast agent, such as Bolus tracking. The controller 28 may also be separate from the C-arm 16 and/or control the rotation of the C-arm 16. For example, the C-arm 16 can move in the direction of arrow A or rotate about the longitudinal axis 12a of the patient 12, allowing anterior or lateral views of the patient 12 to be imaged. Each of these movements involves rotation about a mechanical axis 32 of the C-arm 16. The movements of the imaging device 14, such as the C-arm 16 can be tracked with a tracking device 33.

While the imaging device 14 is shown in FIG. 1 as a C-arm 16, any other alternative 2D, 3D or 4D imaging modality may also be used. For example, any 2D, 3D or 4D imaging device, such as an O-Arm™ imaging device, isocentric fluoroscopy, bi-plane fluoroscopy, ultrasound, computed tomography (CT), multi-slice computed tomography (MSCT), magnetic resonance imaging (MRI), high frequency ultrasound (HFU), positron emission tomography (PET), optical coherence tomography (OCT), intra-vascular ultrasound (IVUS), ultrasound, intra-operative CT or MRI may also be used to acquire 2D, 3D or 4D pre- or post-operative and/or real-time images or patient image data 100 of the patient 12. For example, an intra-operative MRI system, may be used such as the PoleStar® MRI system sold by Medtronic, Inc.

In addition, image datasets from hybrid modalities, such as positron emission tomography (PET) combined with CT, or single photon emission computer tomography (SPECT) combined with CT, could also provide functional image data superimposed onto anatomical data to be used to confidently reach target sites within the patient 12. It should further be noted that the imaging device 14, as shown in FIG. 1, provides a virtual bi-plane image using a single-head C-arm fluoroscope as the imaging device 14 by simply rotating the C-arm 16 about at least two planes, which could be orthogonal planes, to generate two-dimensional images that can be converted to three-dimensional volumetric images. By acquiring images in more than one plane, an icon 103 representing the location of an instrument 52, such as an impacter, stylet, reamer driver, taps, drill, deep-brain stimulator (DBS) probes, cardiac leads or other instrument, or implantable devices introduced and advanced in the patient 12, may be superimposed in more than one view and included in image data 102 displayed on a display 36, as will be discussed.

If the imaging device 14 is employed, patient image data 100 can be forwarded from the controller 28 to a navigation computer and/or processor or workstation 34. It will also be understood that the patient image data 100 is not necessarily first retained in the controller 28, but may also be directly transmitted to the workstation 34. The workstation 34 can include the display 36, a user input device 38 and a control module 101. The workstation 34 can also include or be connected to an image processor, navigation processor, and memory to hold instruction and data. The workstation 34 can provide facilities for displaying the patient image data 100 as an image on the display 36, saving, digitally manipulating, or printing a hard copy image of the received patient image data 100.

The user input device 38 can comprise any device that can enable a user to interface with the workstation 34, such as a touchpad, touch pen, touch screen, keyboard, mouse, wireless mouse, or a combination thereof. The user input device 38 allows a physician or user 39 to provide inputs to control the imaging device 14, via the controller 28, adjust the display settings of the display 36, or control a tracking system 44, as further discussed herein.

The control module 101 can determine the location of a tracking device 58 with respect to the patient space, and can output image data 102 to the display 36. The image data 102 can include an icon 103 that provides an indication of a location of the instrument 52 with respect to the patient space, illustrated on the patient image data 100, as will be discussed herein.

With continuing reference to FIG. 1, the navigation system 10 can further include the electromagnetic navigation or tracking system 44 that includes a localizer, such as a first coil array 46 and/or second coil array 47, the coil array controller 48, a navigation probe interface 50, a device or instrument 52, a patient tracker or first reference frame or dynamic reference frame (DRF) 54, a patient tracker tracker or second reference frame or DRF tracker 54a and one or more tracking devices 58. Other tracking systems can include an optical tracking system 44b, for example the StealthStation® Treon® and the StealthStation® Tria® both sold by Medtronic Navigation, Inc. Further, other tracking systems can be used that include acoustic, radiation, radar, infrared, etc., or hybrid systems, such as a system that includes components of both an electromagnetic and optical tracking system, etc. The instrument 52, the DRF 54 and the DRF tracker 54a can each include tracking device(s) 58.

The tracking device 58 or any appropriate tracking device as discussed herein, can include both a sensor, a transmitter, or combinations thereof and can be indicated by the reference numeral 58. Further, the tracking device 58 can be wired or wireless to provide a signal or emitter or receive a signal from a system. For example, a tracking device 58a can include one or more electromagnetic coil, such as a tri-axial coil, to sense a field produced by the localizing coil array 46 or 47. One will understand that the tracking device(s) 58 can receive a signal, transmit a signal, or combinations thereof to provide information to the navigation system 10, which can be used to determine a location of the tracking device 58. The navigation system 10 can determine a position of the instrument 52, the DRF 54 and the DRF tracker 54a based on the location of the tracking device(s) 58 to allow for accurate navigation relative to the patient 12 in the patient space.

With regard to the optical localizer or tracking system 44b, the optical tracking system 44b can transmit and receive an optical signal, or combinations thereof. An optical tracking device 58b can be interconnected with the instrument 52, or other devices such as the DRF 54 and/or DRF tracker 54a. As generally known, the optical tracking device 58b can reflect, transmit or receive an optical signal to/from the optical localizer or tracking system 44b that can be used in the navigation system 10 to navigate or track various elements. Therefore, one skilled in the art will understand, that the tracking device(s) 58 can be any appropriate tracking device to work with any one or multiple tracking systems.

The coil arrays 46, 47 can transmit signals that are received by the tracking device(s) 58. The tracking device(s) 58 can then transmit or receive signals based upon the transmitted or received signals from or to the coil arrays 46, 47. The coil arrays 46, 47 are shown attached to the operating table 49. It should be noted, however, that the coil arrays 46, 47 can also be positioned at any other location, as well and can also be positioned in the items being navigated. The coil arrays 46, 47 include a plurality of coils that are each operable to generate distinct electromagnetic fields into the navigation region of the patient 12, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference. In addition, representative electromagnetic systems can include the AXIEM™ electromagnetic tracking system sold by Medtronic Navigation, Inc.

The coil arrays 46, 47 can be controlled or driven by the coil array controller 48. The coil array controller 48 can drive each coil in the coil arrays 46, 47 in a time division multiplex or a frequency division multiplex manner. In this regard, each coil can be driven separately at a distinct time or all of the coils can be driven simultaneously with each being driven by a different frequency. Upon driving the coils in the coil arrays 46, 47 with the coil array controller 48, electromagnetic fields are generated within the patient 12 in the area where the medical procedure is being performed, which is again sometimes referred to as patient space. The electromagnetic fields generated in the patient space induce currents in a tracking device(s) 58 positioned on or in the instrument 52, DRF 54 and DRF tracker 54a. These induced signals from the instrument 52, DRF 54 and DRF tracker 54a are delivered to the navigation probe interface 50 and can be subsequently forwarded to the coil array controller 48.

In addition, the navigation system 10 can include a gating device or an ECG or electrocardiogram triggering device, which is attached to the patient 12, via skin electrodes, and in communication with the coil array controller 48. Respiration and cardiac motion can cause movement of cardiac structures relative to the instrument 52, even when the instrument 52 has not been moved. Therefore, patient image data 100 can be acquired from the imaging device 14 based on a time-gated basis triggered by a physiological signal. For example, the ECG or EGM signal may be acquired from the skin electrodes or from a sensing electrode included on the instrument 52 or from a separate reference probe (not shown). A characteristic of this signal, such as an R-wave peak or P-wave peak associated with ventricular or atrial depolarization, respectively, may be used as a reference of a triggering event for the coil array controller 48 to drive the coils in the coil arrays 46, 47. This reference of a triggering event may also be used to gate or trigger image acquisition during the imaging phase with the imaging device 14. By time-gating the image data 102 and/or the navigation data, the icon 103 of the location of the instrument 52 in image space relative to the patient space at the same point in the cardiac cycle may be displayed on the display 36. Further detail regarding the time-gating of the image data and/or navigation data can be found in U.S. Pub. Application No. 2004-00978906, entitled "Navigation System for Cardiac Therapies," filed Nov. 19, 2002, which is hereby incorporated by reference.

The navigation probe interface 50 may provide the necessary electrical isolation for the navigation system 10. The navigation probe interface 50 can also include amplifiers, filters and buffers to directly interface with the tracking device(s) 58 in the instrument 52, DRF 54 and DRF tracker 54a. Alternatively, the tracking device(s) 58, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 50.

The instrument 52 may be any appropriate instrument, such as an instrument for preparing a portion of the patient 12 or an instrument for positioning an implant. The DRF 54 of the tracking system 44 can be coupled to the navigation probe interface 50. The DRF 54 may be coupled to a first portion of the anatomical structure of the patient 12 adjacent to the region being navigated so that any movement of the patient 12 is detected as relative motion between the coil arrays 46, 47 and the DRF 54. For example, as will be discussed, the DRF 54 can be adhesively coupled to the patient 12, however, the DRF 54 could also be mechanically coupled to the patient 12, if desired. The DRF 54 may include any appropriate tracking device(s) 58 used by the navigation system 10. Therefore, the DRF 54 can include an optical tracking device or acoustic, etc. If the DRF 54 is used with an electromagnetic tracking device 58a it can be configured as a pair of orthogonally oriented coils, each having the same centerline or may be configured in any other non-coaxial or co-axial coil configurations, such as a tri-axial coil configuration (not specifically shown).

The DRF tracker 54a of the tracking system 44 can also be coupled to the navigation probe interface 50. The DRF tracker 54a may be coupled to a second portion of the anatomical structure of the patient 12 substantially opposite the DRF 54, so that any movement of the DRF 54 is detected as relative motion between the DRF 54 and the DRF tracker 54a. It will be understood, however, that the DRF tracker 54a could be positioned at any desired location with respect to the DRF 54, and thus, the position of the DRF tracker 54a relative to the DRF 54 should not be limited to substantially opposite the DRF 54, as this location is merely exemplary. For example, the DRF 54 and DRF tracker 54a could each be coupled to the same side of the anatomy, if desired. In addition, the DRF tracker 54a can be adhesively coupled to the patient 12, however, the DRF tracker 54a could also be mechanically coupled to the patient 12. The DRF tracker 54a may include any appropriate tracking device(s) 58 used by the navigation system 10. Therefore, the DRF tracker 54a can include an electromagnetic tracking device 58a, an optical tracking device 58b, or acoustic, etc. If the DRF tracker 54a is used with an electromagnetic tracking device 58a, it can be configured as a pair of orthogonally oriented coils, each having the same center or may be configured in any other non-coaxial or co-axial coil configurations (not specifically shown).

Briefly, the navigation system 10 operates as follows. The navigation system 10 creates a translation map between all points in the radiological image generated from the imaging device 14 in image space and the corresponding points in the anatomical structure of the patient 12 in patient space. After this map is established, whenever a tracked instrument, such as the instrument 52 is used, the workstation 34 in combination with the coil array controller 48 and the controller 28 uses the translation map to identify the corresponding point on the pre-acquired image or atlas model, which is displayed on display 36. This identification is known as navigation or localization. The icon 103 representing the localized point or instruments 52 can be shown as image data 102 on the display 36.

To enable navigation, the navigation system 10 must be able to detect both the position of the anatomical structure of the patient 12 and the position of the instrument 52. Knowing the location of these two items allows the navigation system 10 to compute and display the position of the instrument 52 in relation to the patient 12 on the display 36. The tracking system 44 can be employed to track the instrument 52 and the anatomical structure simultaneously.

The tracking system 44, if using an electromagnetic tracking assembly, essentially works by positioning the coil arrays 46, 47 adjacent to the patient space to generate a low-energy electromagnetic field generally referred to as a navigation field. Because every point in the navigation field or patient space is associated with a unique field strength, the tracking system 44 can determine the position of the instrument 52 by measuring the field strength at the tracking device 58 location. The DRF 54 can be fixed to the patient 12 to identify a first location of the patient 12 in the navigation field, and the DRF tracker 54a can be coupled to the anatomy to identify a second location of the patient 12. The DRF 54 and the DRF tracker 54a can be used to detect unplanned motion of the DRF 54 or DRF tracker 54a relative to the anatomy, as will be discussed. The tracking system 44 can continuously recompute the relative position of the DRF 54, the DRF tracker 54a and the instrument 52 during localization and relate this spatial information to patient registration data to enable image guidance of the instrument 52 within and/or relative to the patient 12.

Patient registration is the process of determining how to correlate the position of the instrument 52 relative to the patient 12 to the position on the diagnostic or pre-acquired images. To register the patient 12, a physician or user 39 may use point registration by selecting and storing particular points from the pre-acquired images and then touching the corresponding points on the anatomical structure of the patient 12 with a pointer probe. The navigation system 10 analyzes the relationship between the two sets of points that are selected and computes a match, which correlates every point in the patient image data 100 with its corresponding point on the anatomical structure of the patient 12 or the patient space, as discussed herein. The points that are selected to perform registration are the fiducial markers 60, such as anatomical landmarks. Again, the landmarks or fiducial markers 60 are identifiable on the images and identifiable and accessible on the patient 12. The fiducial markers 60 can be artificial markers that are positioned on the patient 12 or anatomical landmarks that can be easily identified in the patient image data 100. The artificial landmarks, such as the fiducial markers 60, can also form part of the DRF 54, such as those disclosed in U.S. Pat. No. 6,381,485, entitled "Registration of Human Anatomy Integrated for Electromagnetic Localization," issued Apr. 30, 2002, herein incorporated by reference.

The navigation system 10 may also perform registration using anatomic surface information or path information as is known in the art. The navigation system 10 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 60/465,615, entitled "Method and Apparatus for Performing 2D to 3D Registration" filed on Apr. 25, 2003, hereby incorporated by reference.

In order to maintain registration accuracy, the navigation system 10 continuously tracks the position of the patient 12 during registration and navigation. This is because the patient 12, DRF 54, the DRF tracker 54a and coil arrays 46, 47 may all move with respect to one another during the procedure, even when this movement is not desired. Alternatively the patient 12 may be held immobile once the registration has occurred, such as with a head frame (not shown). Therefore, if the navigation system 10 did not track the position of the patient 12 or area of the anatomy, any patient movement after image acquisition would result in inaccurate navigation within that image. The DRF 54 allows the tracking system 44 to register and track the anatomy, while the DRF tracker 54a can allow the tracking system 44 to track the DRF 54 across from the target anatomy. Because the DRF 54 can be coupled to the patient 12, any movement of the anatomical structure of the patient 12 or the coil arrays 46, 47 can be detected as the relative motion between the coil arrays 46, 47 and the DRF 54. The DRF tracker 54a can be coupled to the anatomical structure of the patient 12 substantially opposite the DRF 54, and any movement of the anatomical structure or DRF 54 is detected as relative motion between the DRF 54 and the DRF tracker 54a, as will be discussed herein. Both the relative motion of the coil arrays 46, 47 and the DRF 54 and DRF tracker 54a can be communicated to the coil array controller 48, via the navigation probe interface 50, which can update the registration correlation to thereby maintain accurate navigation.

The navigation system 10 can be used according to any appropriate method or system. For example, pre-acquired images, atlas or 3D models may be registered relative to the patient 12 and the patient space. Generally, the navigation system 10 allows the images on the display 36 to be registered and to accurately display the real time location of the various instruments, such as the instrument 52, and other appropriate items, such as DRF 54 and DRF tracker 54a. In addition, the DRF 54 may be used to ensure that any planned or unplanned movement of the patient 12 or the coil arrays 46, 47 can be determined and used to correct the image data 102 on the display 36. The DRF tracker 54a can be used to ensure that any unplanned movement of the DRF 54 relative to the patient 12 can be determined by the navigation system 10. As will be discussed, the operator 39 can be notified, via any suitable means, such as the display 36, of any unacceptable unplanned movement of the DRF 54 relative to the patient 12. Thus, the DRF tracker 54a can be used to ensure that navigation is accurate, while also notifying the operator 39 of undesirable motion of the DRF 54, as will be discussed.

In this regard, with reference to FIG. 2A, in one exemplary surgical procedure, such as a spinal procedure, a first patient tracker or first reference frame or DRF 54 can be coupled to the anatomy of the patient 12 at a first location, such as adjacent to a spine 12b of the patient 12. Generally, a patient tracker tracker or second reference frame or DRF tracker 54a can be coupled opposite the DRF 54 at a second location, and for example, can be coupled to a chest of the patient 12, such as to a sternum 12c of the patient 12. In one example, the DRF 54 and the DRF tracker 54a can be adhesively coupled to the patient 12, however, it will be understood that the DRF 54 and/or the DRF tracker 54a could be coupled to the anatomy of the patient 12 through any appropriate technique, such as through a mechanical fastening means (fixation screw, suture, helix, etc.), and can be coupled to any suitable portion of the anatomy such as skin, bone, soft tissue, etc. Further, the DRF 54 and/or the DRF tracker 54a can be indirectly coupled to the anatomy of the patient 12, for example, by attaching the DRF 54, and/or DRF tracker 54a to the operating table 49.

As each of the DRF 54 and the DRF tracker 54a can include the tracking device 58, each of the DRF 54 and the DRF tracker 54a can have known positions and orientations in the patient space. The positions and orientations of the DRF 54 and DRF tracker 54a can comprise coordinate locations of the DRF 54 and DRF tracker 54a in the navigation field generated by the coil arrays 46, 47, as the tracking device 58 associated with each of the DRF 54 and DRF tracker 54a measure unique field strengths. Generally, the DRF 54 and DRF tracker 54a are designed such that a six degrees of freedom transformation can be computed within the navigation field, and thus, the coordinate locations of the DRF 54 and DRF tracker 54a can be determined using a mathematical transform, such as a rigid body transformation, for example.

Based on the signal received from the tracking device 58, a mathematical transformation can determine a position and orientation or coordinate location for each of the DRF 54 and DRF tracker 54a. Further, given the first coordinate location for each of the DRF 54 and DRF tracker 54a, a difference existing between the coordinate locations of the DRF 54 and DRF tracker 54a can be computed. Based on the difference between the coordinate locations, the control module 101 can determine if registration is accurate.

In this regard, any change in the position and/or orientation of the DRF 54 and/or DRF tracker 54a can result in a change in the coordinate locations of the DRF 54 and/or DRF tracker 54a. This change in the coordinate locations of the DRF 54 and/or DRF tracker 54a can result in a change in the relative difference existing between the DRF 54 and DRF tracker 54a. By monitoring the relative difference existing between the DRF 54 and DRF tracker 54a, the control module 101 can determine if the DRF 54 and DRF tracker 54a have moved in an acceptable manner. For example, if the change in the relative difference is substantially cyclic, such that the relative difference changes in about the same amount in a rhythmic manner, the movement of the DRF 54 or DRF tracker 54a can be acceptable due to respiration. The cyclic motion can similarly be classified as acceptable due to cardiac motion.

If there is a change in the relative difference existing between the DRF 54 and DRF tracker 54a due to movement of the DRF 54 and/or DRF tracker 54a, which is not acceptable, then the control module 101 can determine whether to disable the use of the navigation system 10 by the operator, or can compensate and correct for the motion or movement of the DRF 54 and/or DRF tracker 54a relative to the anatomy.

Figure 2B:
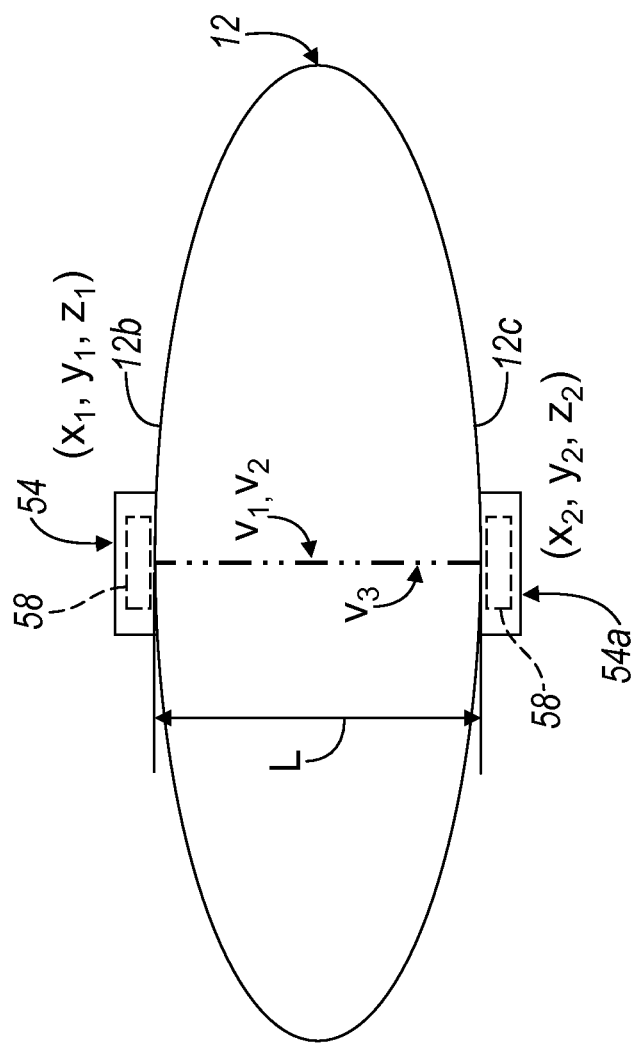
FIG. 2B is a simplified cross-sectional illustration of the patient of FIG. 2A in which the first reference frame is directly opposite the second reference frame.

For illustration purposes, the following provides simplified examples of acceptable and unacceptable movement of the DRF 54 and DRF tracker 54a. It will be understood that the following examples are for illustration purposes only, and are not intended to limit the present teachings to applications involving only three degrees of freedom. In this example, as illustrated in FIG. 2A, the DRF 54 can have coordinates $(x_1, y_1, z_1)$ and the DRF tracker 54a can have coordinates $(x_2, y_2, z_2)$. In addition, each of the DRF 54 and the DRF tracker 54a can include a vector v that can be normal to an exterior surface of the anatomy of the patient 12 from a center C of the DRF 54 and DRF tracker 54a. As illustrated, the DRF 54 can include a normal vector $v_1$, and the DRF tracker 54a can include a normal vector $v_2$. Further, a vector $v_3$ can be computed relative to the coordinate positions $(x_1, y_1, z_1)$ of the DRF 54 and the coordinate positions $(x_2, y_2, z_2)$ of the DRF tracker 54a, as shown in FIG. 2A. In cases where the DRF 54 is positioned about directly opposite the DRF tracker 54a, the normal vectors $v_1$, $v_2$ can have a length $L_1$ and $L_2$, respectively, which can be about equal to a length L of the vector $v_3$ between the DRF 54 and the DRF tracker 54a, as shown in FIG. 2B. In cases, however, where the DRF 54 is not positioned about directly opposite from the DRF tracker 54a, such as when the DRF 54 is positioned adjacent to a spine of the patient 12 at a heart level, then the vector $v_3$ between the DRF 54 and the DRF tracker 54a can have a length L that can be generally larger than the lengths $L_1$, $L_2$ of the normal vectors $v_1$, $v_2$ through the anatomy. In addition, the vector $v_3$ can be formed at an angle A relative to the vectors $v_1$, $v_2$ as shown in FIG. 2A.

Figure 3:
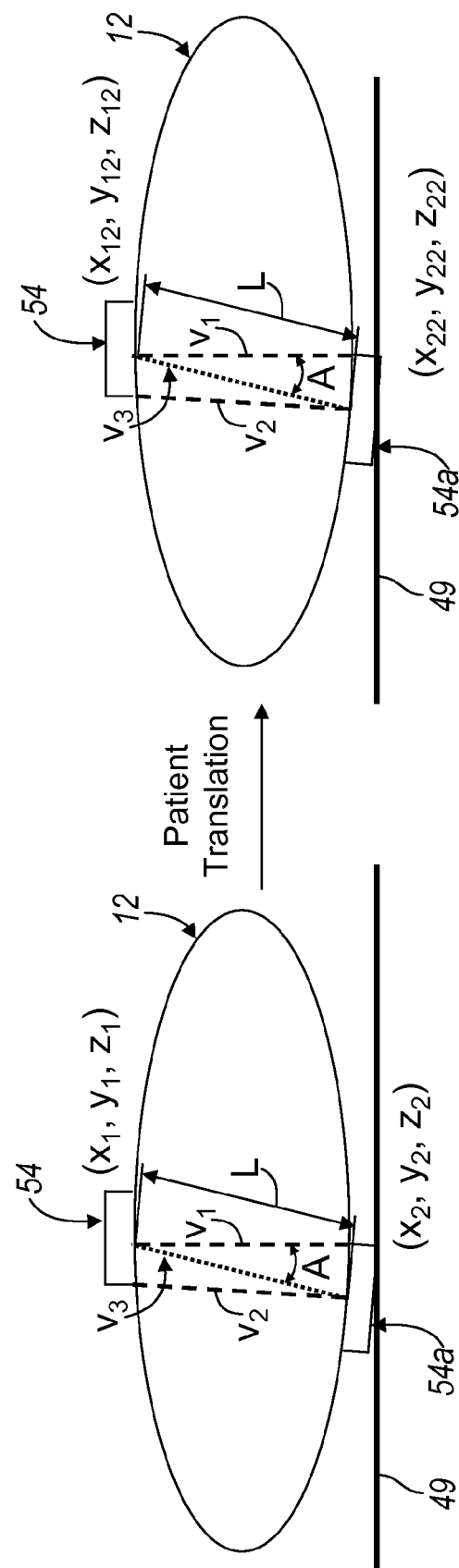
FIG. 3 is a simplified cross-sectional illustration of the patient of FIG. 2A before and after a translational movement.

As the length L and angle A of the vector $v_3$ between the DRF 54 and the DRF tracker 54a can be known, the length L and angle A of the vector $v_3$ can be used to determine if the relative motion between the DRF 54 and the DRF tracker 54a (i.e. the relative difference now existing between the DRF 54 and DRF tracker 54a) is acceptable. In this regard, as schematically illustrated in FIG. 3, if the patient 12 shifts or translates during the surgical procedure such that both the DRF 54 and the DRF tracker 54a move with the patient 12, then the length L and angle A of the vector $v_3$ can remain substantially equal to the length L and angle A of the vector $v_3$ prior to the movement of the patient 12. Similarly, as the DRF 54 and the DRF tracker 54a have not moved relative to each other or the patient 12, the relative difference existing between the coordinate locations of the DRF 54 and DRF tracker 54a has also not changed. As the length L and angle A of the vector $v_3$ prior to the movement of the patient 12 can be about equal to the length L and angle A of the vector $v_3$ after the movement of the patient 12, it can be determined that the DRF 54 and/or DRF tracker 54a have not moved relative to the anatomy, and thus, the registration of the anatomy can be accurate even after the movement of the patient 12. In other words, during a translation of the patient 12, both the DRF 54 and the DRF tracker 54a can move with the patient 12, but must always move the same relative to each other (i.e., no change in the relative difference existing between the coordinate locations of the DRF 54 and DRF tracker 54a) to maintain registration accuracy. As the DRF 54 and the DRF tracker 54a can move the same relative to each other, there can be no change in the difference existing between the first coordinate location of the DRF 54 and DRF tracker 54a and the second coordinate location of the DRF 54 and DRF tracker 54a, and thus, this movement can be considered acceptable.

Figure 4:
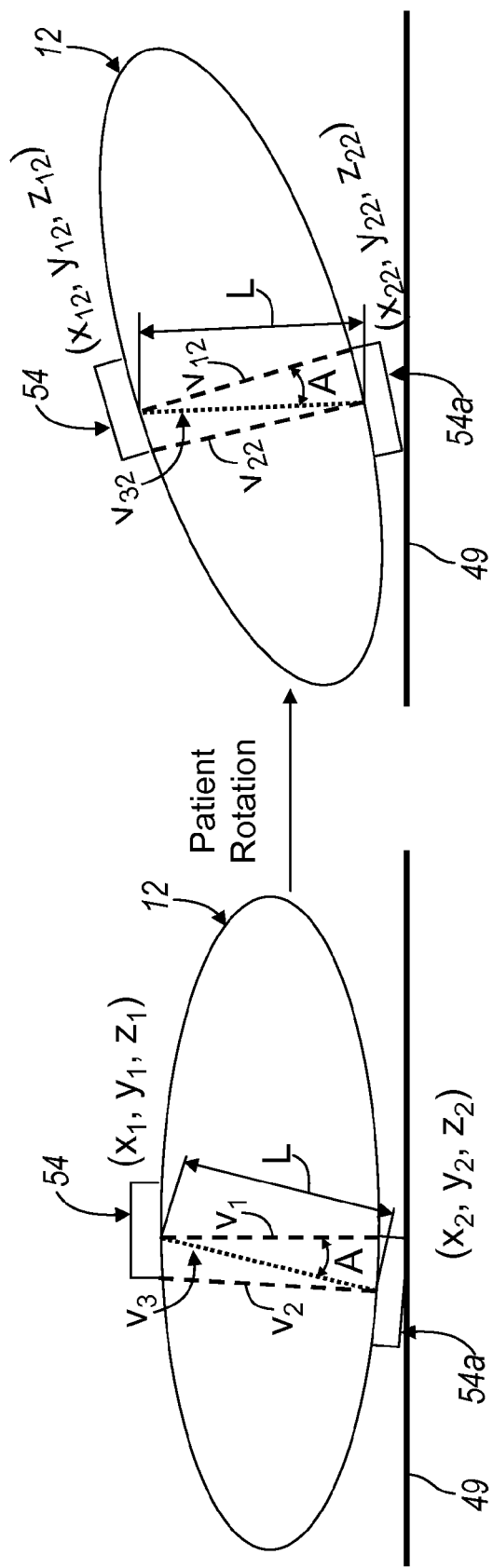
FIG. 4 is a simplified cross-sectional illustration of the patient of FIG. 2A before and after a rotational movement.

In another instance, as schematically illustrated in FIG. 4, if the patient 12 rotates during the surgical procedure such that both the DRF 54 and the DRF tracker 54a move with the patient 12, then the length L and angle A of the vector $v_3$ can remain substantially equal to the length L of the vector $v_3$ prior to the movement of the patient 12. In this regard, during a rotation of the patient, the coordinate position or locations of the DRF 54 and the DRF tracker 54a and the normal vectors $v_1$, $v_2$ of the DRF 54 and DRF tracker 54a can change, but the relative difference existing between the coordinate locations DRF 54 and DRF tracker 54a does not change. Further, using the simplified example, the length L and angle A of the vector $v_3$ between the DRF 54 and the DRF tracker 54a remains substantially the same. As the length L and angle A of the vector $v_3$ prior to the movement of the patient 12 can be about equal to the length L and angle A of the vector $v_3$ after the movement of the patient 12, it can be determined that the DRF 54 has not moved relative to the patient 12, and thus, the registration of the patient 12 can be accurate even after this movement of the patient 12. In other words, as the difference existing between the coordinate locations of the DRF 54 and the DRF tracker 54a in the patient space does not change, this movement of the DRF 54 and DRF tracker 54a can be considered acceptable.

Figure 5:
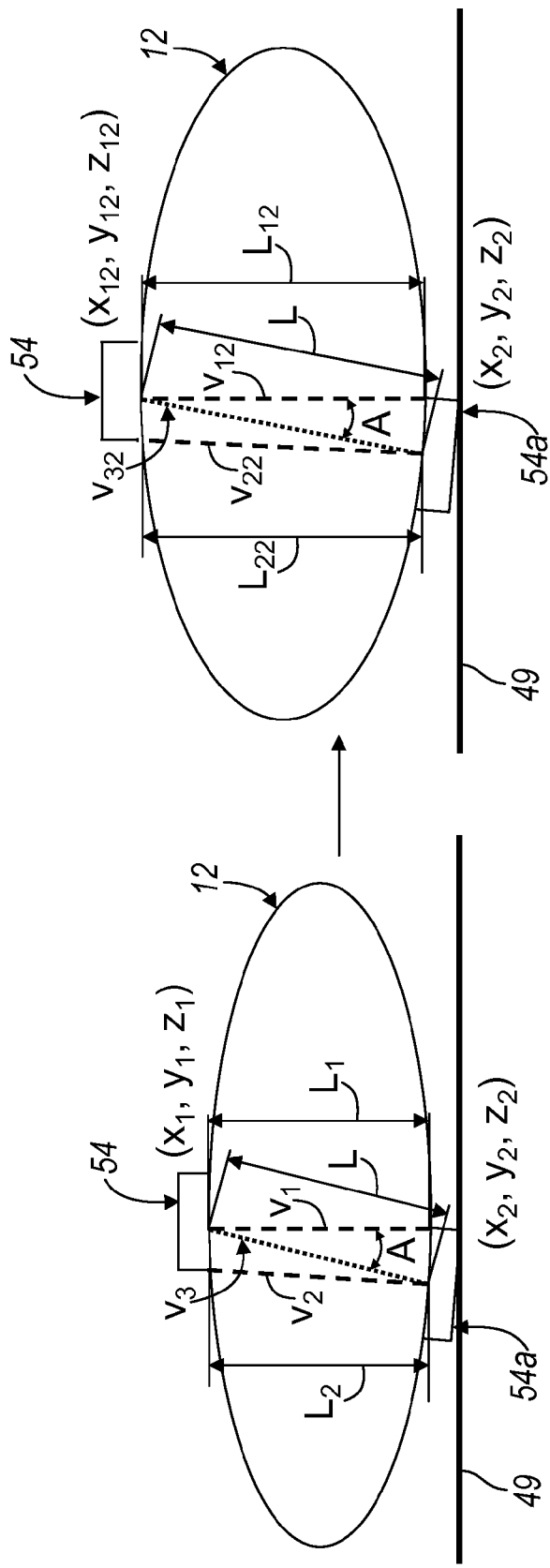
FIG. 5 is a simplified cross-sectional illustration of the patient of FIG. 2A before and after respiration.

Further, the respiration of the patient 12 can be accounted for and considered acceptable motion as cyclically, there is a predictable change in the difference existing between the coordinate locations of the DRF 54 and DRF tracker 54a. In other words, the respiration of the patient 12 can be identified and considered acceptable motion based on a cyclic change in the relative difference between the coordinate locations of the DRF 54 and DRF tracker 54a, or in the simplified example, the length L of the vector $v_3$ between the DRF 54 and the DRF tracker 54a. In this regard, during respiration, as the DRF tracker 54a can be coupled to the chest of the patient 12, the DRF tracker 54a can move relative to the DRF 54, and the movement of the chest can cause the relative difference between the coordinate locations of the DRF 54 and DRF tracker 54a to change cyclically, or in the simplified example, this relative movement can cause a length $L_1$, $L_2$ of the normal vectors $v_1$, $v_2$ to change as schematically illustrated in FIG. 5. This relative motion between the DRF tracker 54a and the DRF 54 can also cause the length L of the vector $v_3$ to change. Further, the respiration of the patient 12 can have a known frequency, for example about 0.25 Hertz (Hz). Thus, the relative motion between the DRF 54 and the DRF tracker 54a can be determined acceptable if the relative difference between the coordinate locations, or as in the example, the lengths L, $L_1$, $L_2$ of the vectors $v_1$, $v_2$, $v_3$, and the coordinate location of the DRF tracker 54a change in a pattern that corresponds to the frequency of the respiration.

Figure 6:
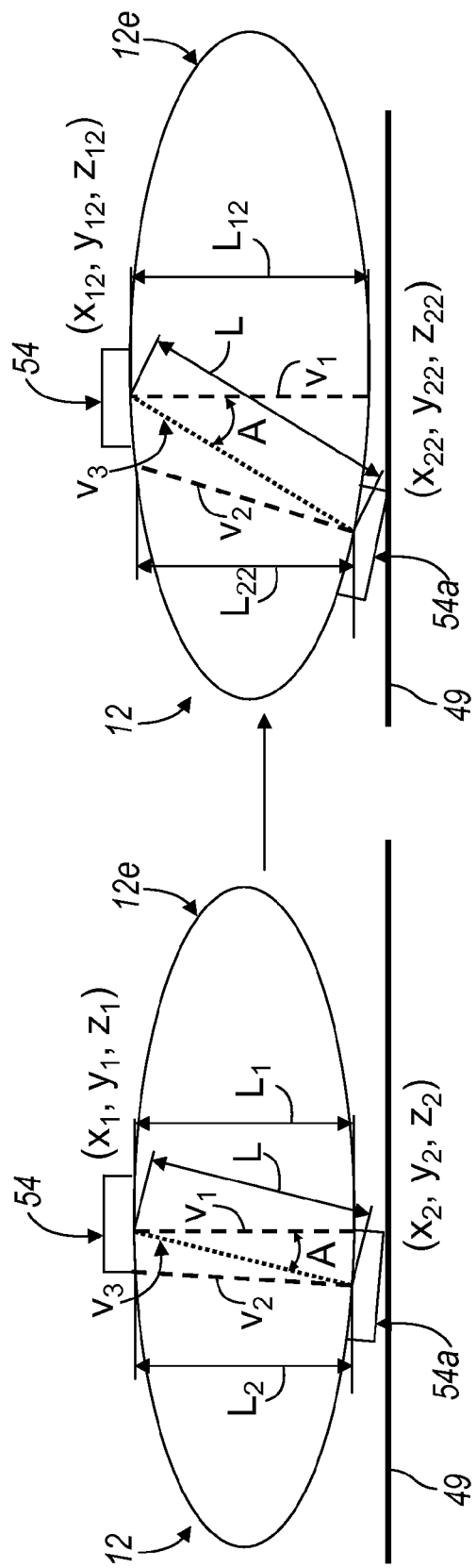
FIG. 6 is a simplified cross-sectional illustration of the patient of FIG. 2A before and after a portion of skin on the patient shifts.

A change in the difference existing between the coordinate locations of the DRF 54 and DRF tracker 54a can identify unacceptable movement between the DRF 54 and the DRF tracker 54a. For example, as schematically illustrated in FIG. 6, if the DRF 54 and the DRF tracker 54a are adhesively coupled to skin 12e of the patient 12, and the skin 12e of the patient 12 moves relative to an internal anatomical structure of the patient 12, registration can become inaccurate due to this skin shift. In this regard, skin shift can cause one of the DRF 54 or the DRF tracker 54a to move relative to the other. The movement of the DRF 54 or the DRF tracker 54a can result in a new coordinate location (position and/or orientation) for one of the DRF 54 and the DRF tracker 54a, which in turn, can result in a change in the relative difference existing between the coordinate locations of the DRF 54 and DRF tracker 54a. In continuing with the example of FIG. 6, this new coordinate location can also result in a new length $L_1$ or $L_2$ for the normal vector $v_1$, $v_2$, of the respective DRF 54 or DRF tracker 54a. Further, the new coordinate location for the DRF 54 or DRF tracker 54a can result in a new length L for the vector $v_3$.

If the change in the relative difference existing between the coordinate locations of the DRF 54 and DRF 54a, or in the example, the new length L of the vector $v_3$ does not change cyclically, as in the case of respiration or cardiac motion, it can be determined that one of the DRF 54 or the DRF tracker 54a has moved relative to an anatomical structure or organ of the patient 12 in an unacceptable position, such that registration is no longer accurate. If it is determined that one of the DRF 54 or DRF tracker 54a has moved relative to the patient 12 such that registration is no longer accurate, then the control module 101 can update the operator 39, via the display 36 to indicate that registration is inaccurate, for example, or could update the registration to compensate for the movement of the DRF 54 or DRF tracker 54a, if desired, as will be discussed.

For example, the navigation system 10 can account for unacceptable motion of the DRF 54 or DRF tracker 54a by analyzing the change in the relative difference between the coordinate locations of the DRF 54 and DRF tracker 54a, and then determining which of the DRF 54 and DRF tracker 54a has moved. The one of the DRF 54 or DRF tracker 54a that has not moved can then provide the true location of the respective DRF 54 or DRF tracker 54a to the navigation system 10 in order to correct and update the registration information. As the coil arrays 46, 47 generally do not move during the procedure, the stationary one of DRF 54 or DRF tracker 54a can be detected by the coil array controller 48 based on the unique field strength sensed by the tracking device 58 associated with the DRF 54 and/or DRF tracker 54a.

Figure 7:
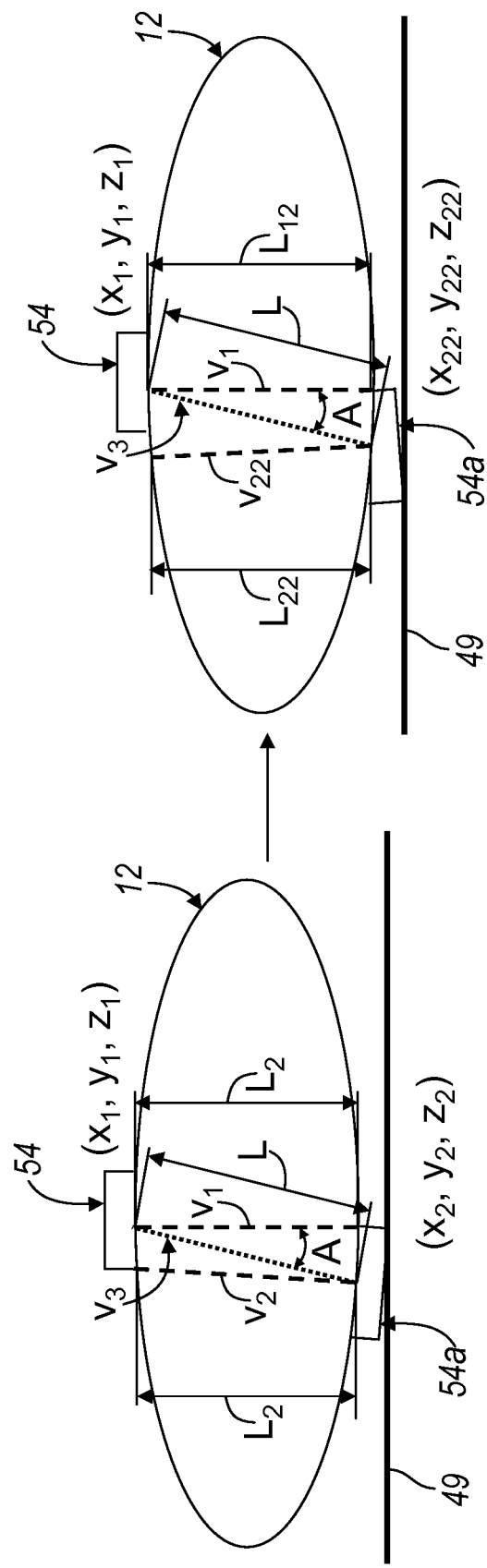
FIG. 7 is a simplified cross-sectional illustration of the patient of FIG. 2A before and after the second reference frame becomes slightly uncoupled from the patient.

In another example, as schematically illustrated in FIG. 7, if a portion of the DRF 54 or DRF tracker 54a becomes uncoupled from the patient 12, then the coordinate location (position and orientation) of the uncoupled DRF 54 or DRF tracker 54a can change. This movement can cause a change in the relative difference existing between the coordinate locations of the DRF 54 and DRF tracker 54a, or as illustrated in FIG. 7 a change in a length L and/or angle A of the vector $v_3$ can indicate this movement of the DRF 54 or DRF tracker 54a. Further, the uncoupling of the DRF 54 or DRF tracker 54a can change the length $L_1$, $L_2$ of the normal vector $v_1$, $v_2$, which can further indicate the movement of the respective DRF 54 or DRF tracker 54a. If it is determined that the DRF 54 or DRF tracker 54a has moved relative to the anatomical structure or organ of the patient 12 such that registration is no longer accurate, then the control module 101 can update the operator 39, or could update the registration to compensate for the movement.

Figure 8:
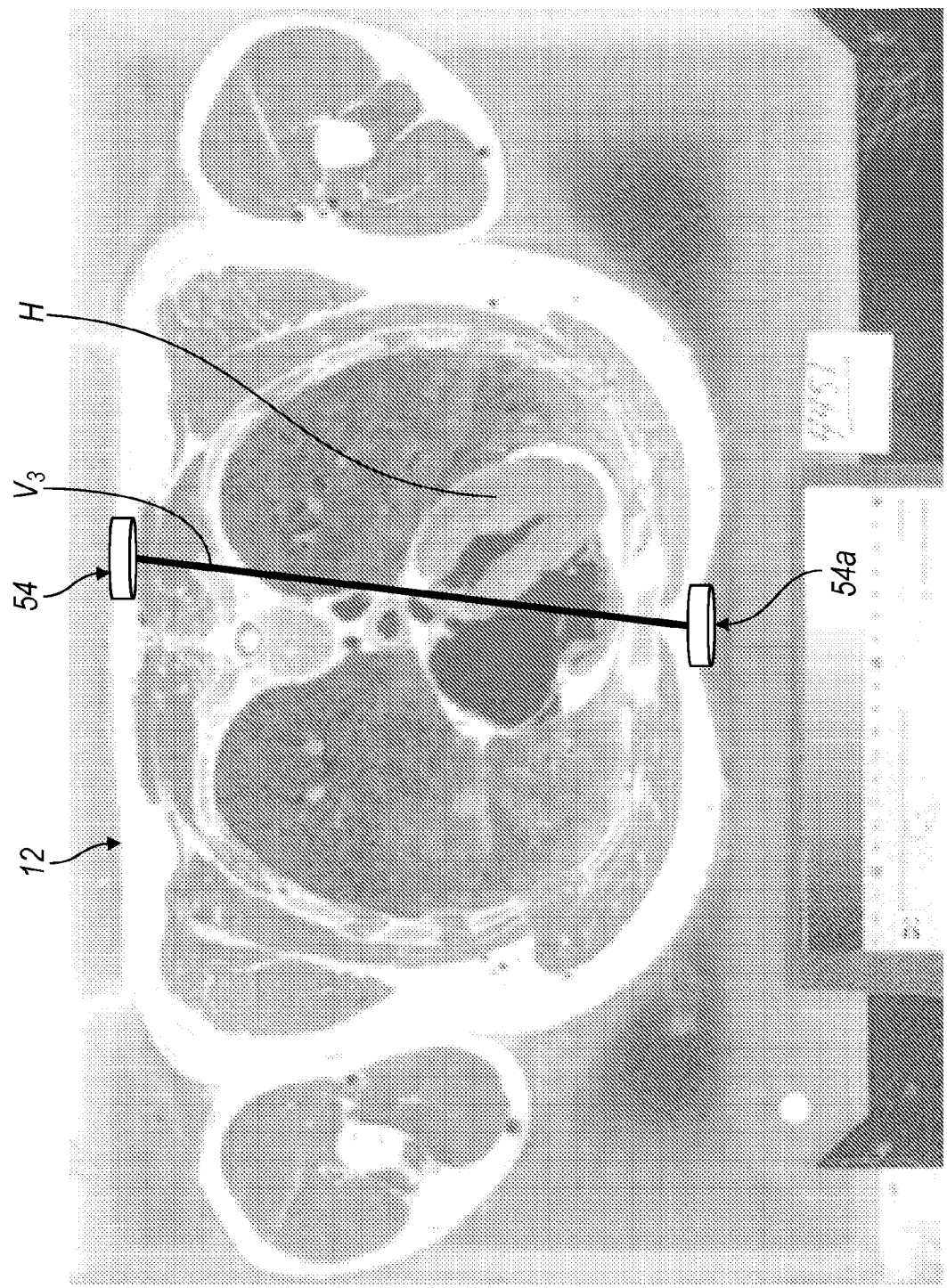
FIG. 8 is a simplified cross-sectional illustration of the patient of FIG. 1, taken along line 2-2 of FIG. 1, which shows a graphical representation of a vector drawn between the first reference frame and the second reference frame.
Figure 9:
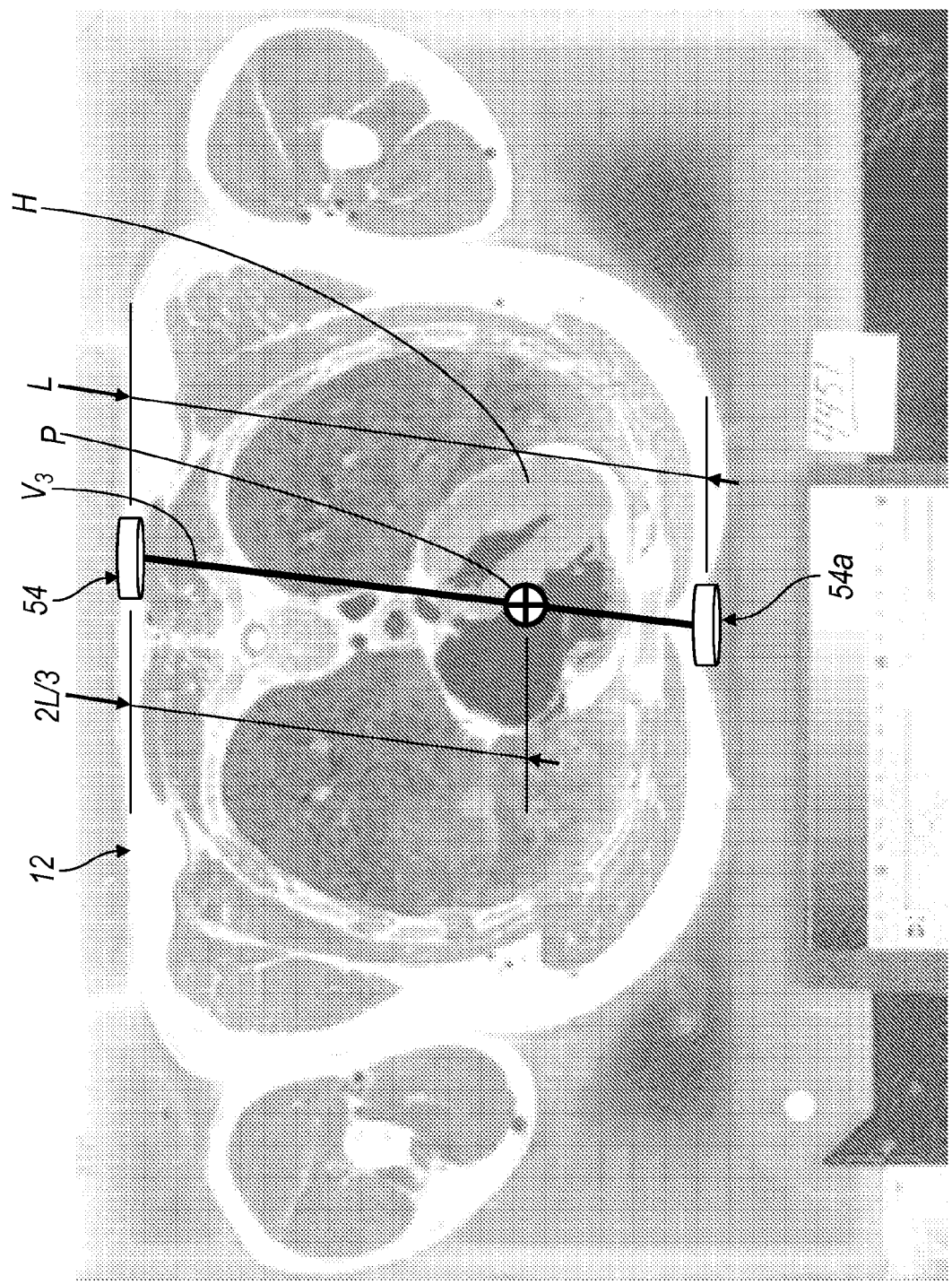
FIG. 9 is a simplified cross-sectional illustration of the patient of FIG. 1, taken along line 2-2 of FIG. 1, which shows a graphical representation of a point selected on the vector drawn between the first reference frame and the second reference frame.

With regard to FIG. 8, in one example, in order to track the movement of the DRF 54 with the DRF tracker 54a, the operator 39 can establish, via the user input device 38, an acceptance volume for the movement of the DRF 54 relative to the anatomy. In this regard, a vector $v_3$ can be drawn between the origin or initial coordinate locations of the DRF 54 and DRF tracker 54a. The vector $v_3$ can be displayed on the patient image data 100 on the display 36. As shown in FIG. 9, the operator 39 can use the user input device 38 to select a desired point P on the vector $v_3$ that is through or adjacent to a surgical site, for example, a point about two-thirds the length L of the vector $v_3$, adjacent to a heart H, which in this example is the surgical site or region of interest.

Figure 10:
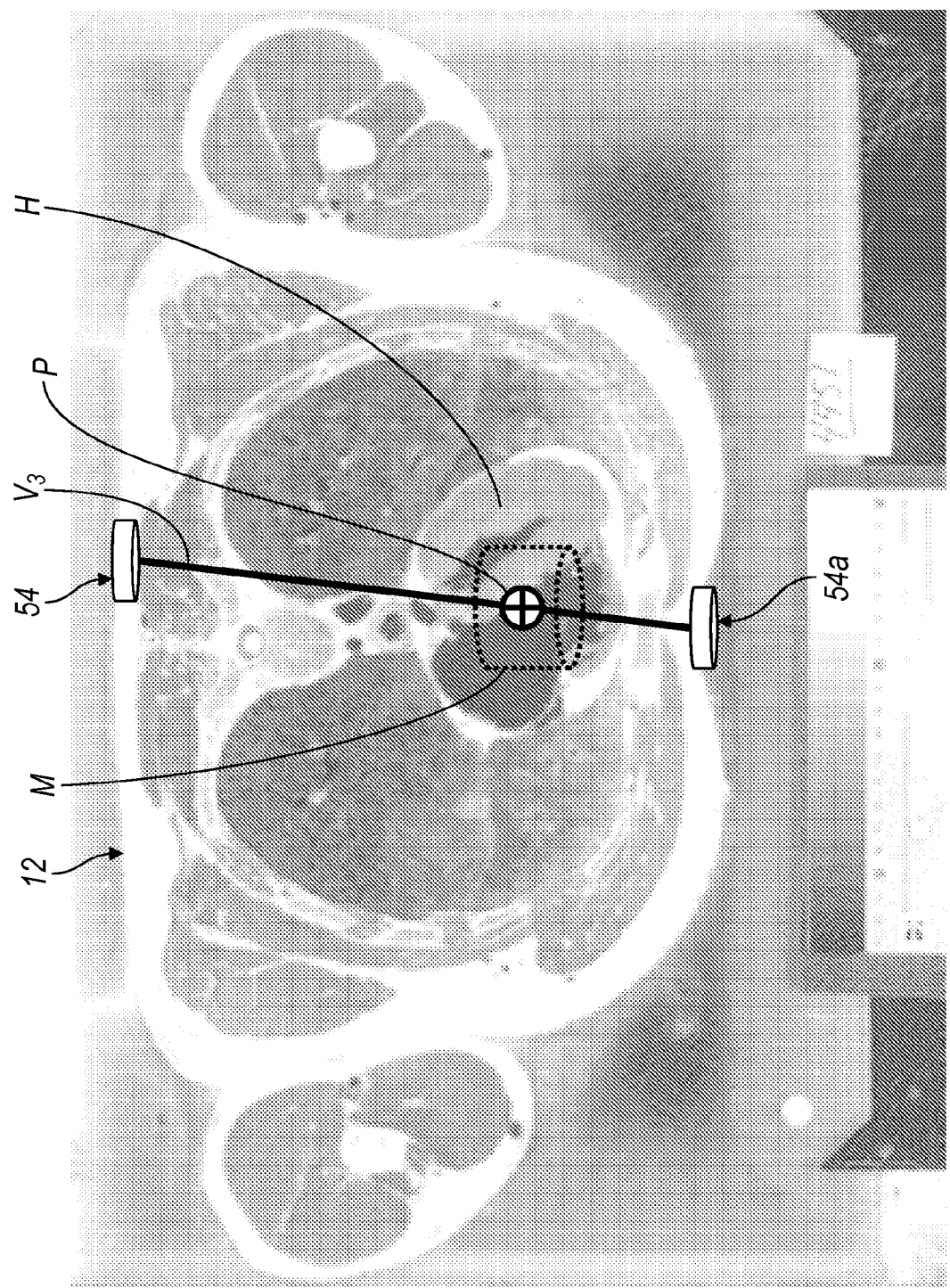
FIG. 10 is a simplified cross-sectional illustration of the patient of FIG. 1, taken along line 2-2 of FIG. 1, which shows a graphical representation of a boundary volume formed about the point selected in FIG. 9.
Figure 11:
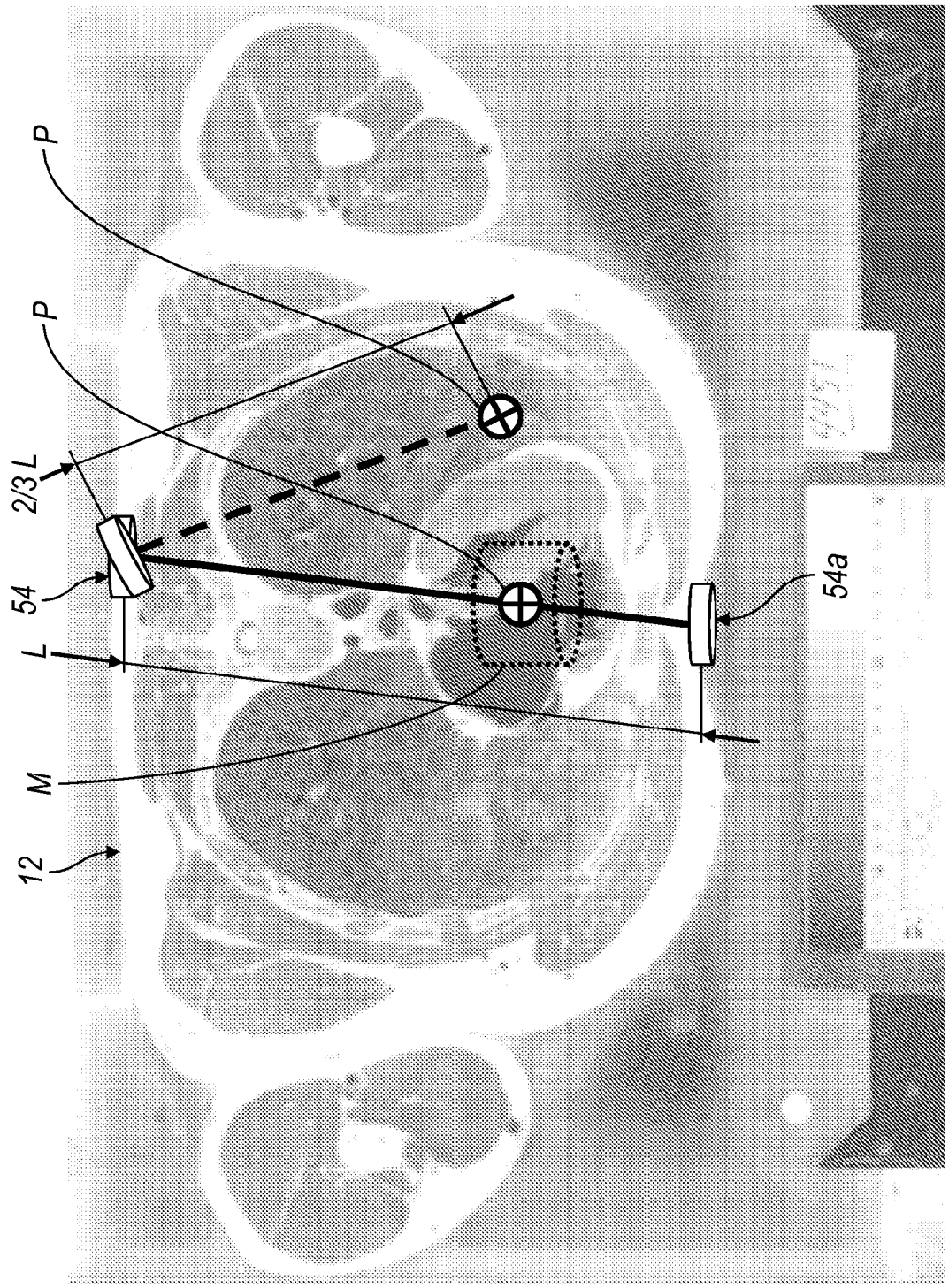
FIG. 11 is a simplified cross-sectional illustration of the patient of FIG. 1, taken along line 2-2 of FIG. 1, which shows a graphical representation of unacceptable movement of the first reference frame.

With reference to FIG. 10, the operator 39 can then select a desired volume M about the point P in which the translation of the point P on the vector $v_3$ is acceptable. In other words, the defined volume M can establish a boundary volume for the point P. For example, if the vector $v_3$ is drawn between the DRF 54 and DRF tracker 54a and the point P at two-thirds the length L of the vector $v_3$ is outside the volume M, then the movement of the DRF 54 and/or DRF tracker 54a is unacceptable, as illustrated in FIG. 11.

Figure 10A:
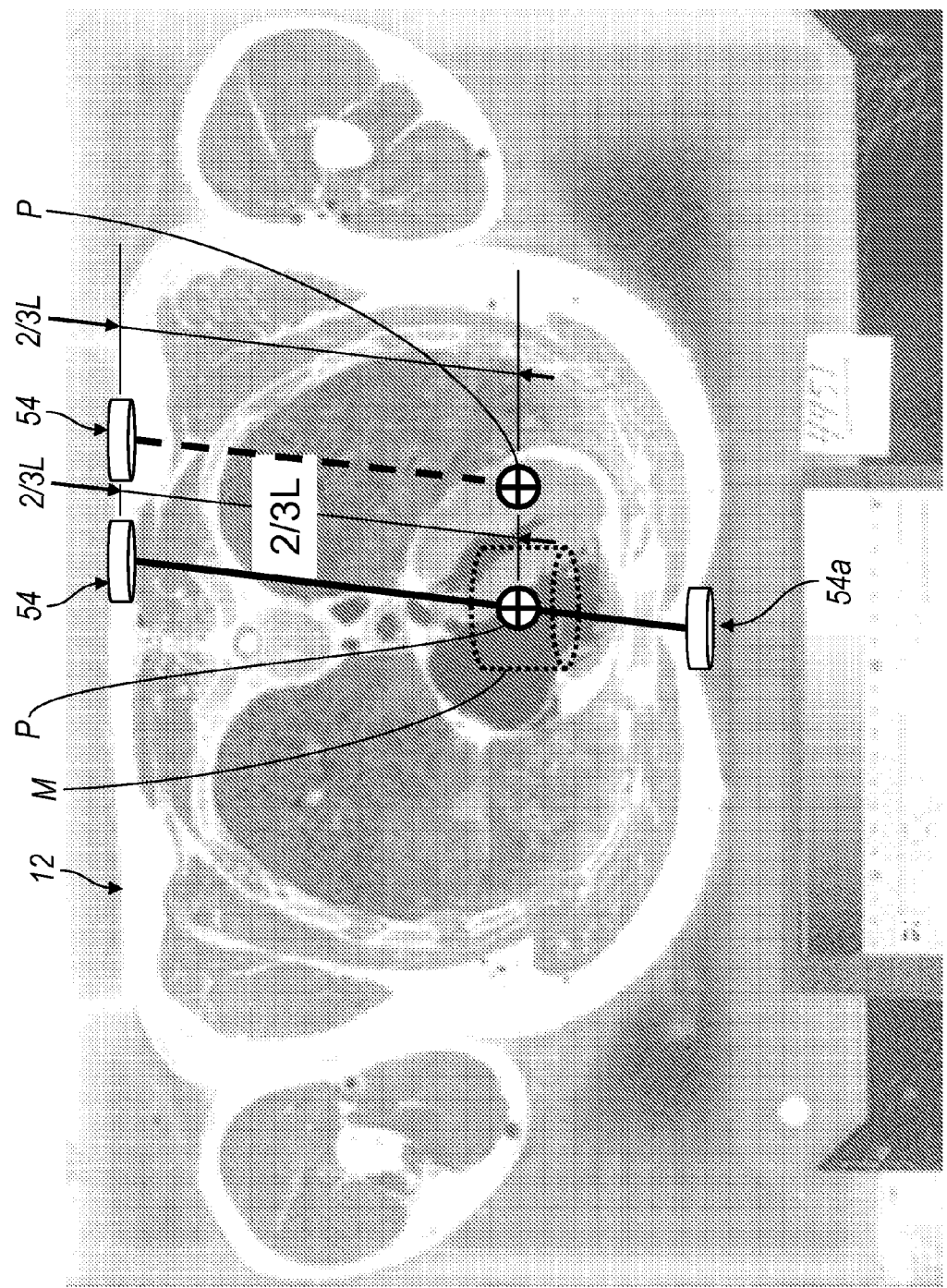
FIG. 10A is a simplified cross-sectional illustration of the patient of FIG. 1, taken along line 2-2 of FIG. 1, which shows a graphical representation of unacceptable movement of the first reference frame.

In this regard, the control module 101 can determine a location of the point P based on the tracking of the DRF 54 alone, and can determine a location of the point P based on the tracking of the DRF tracker 54a alone. If, based on either the tracking of the DRF 54 or the DRF tracker 54a, the point P is outside the volume M, as illustrated in FIG. 10A, then it can be determined that registration is no longer accurate. If it is determined that the DRF 54 or DRF tracker 54a has moved relative to the patient 12 such that registration is no longer accurate, then the control module 101 can update the operator 39, or could update the registration to compensate for the movement.

Figure 10B:
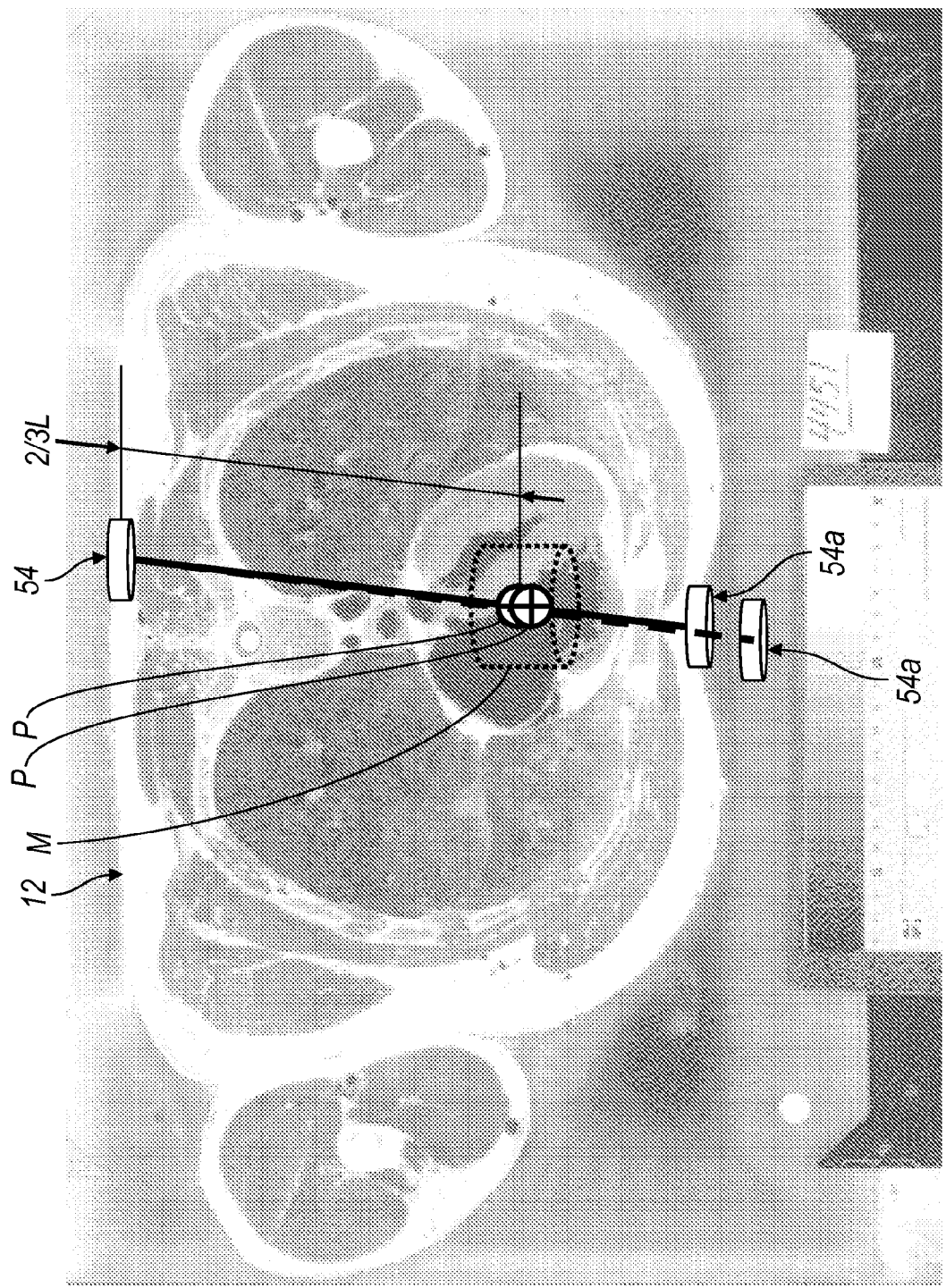
FIG. 10B is a simplified cross-sectional illustration of the patient of FIG. 1, taken along line 2-2 of FIG. 1, which shows a graphical representation of acceptable movement of the second reference frame due to respiration.

Further, the user can establish the volume M such that the volume M includes any angular variation in the location of the point P due to the respiration of the patient 12. In a cardiac procedure, as illustrated in FIG. 10B, the DRF tracker 54a can be coupled to the sternum, and thus, the DRF tracker 54a can move with every respiratory cycle. Accordingly, the location of the point P based on the tracking of the DRF tracker 54a can vary cyclically, and generally, the location of the point P can translate along the vector $v_3$ with the upward movement of the sternum, and thus, the DRF tracker 54a during respiration. Typically, the maximum peak-to-peak displacement of the point P due to respiration ranges from about 2 mm to about 10 mm. As the volume M can be sized to account for this translation of the point P along the vector $v_3$, this movement of the DRF tracker 54a can be considered acceptable motion by the control module 101, and thus, registration will still be considered accurate even with this movement. In addition, if desired, the movement of the DRF tracker 54a can be used to trigger image acquisition and/or the display navigation of data on the display 36.

Figure 12:
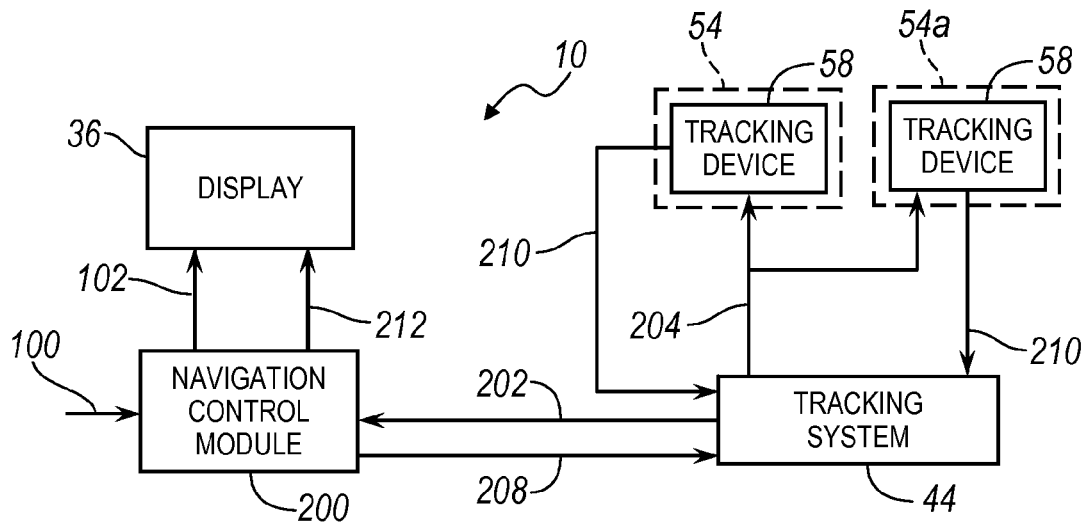
FIG. 12 is a simplified block diagram illustrating the navigation system of FIG. 1.

With reference now to FIG. 12, a simplified block diagram schematically illustrates an exemplary navigation system 10 for implementing the control module 101. The navigation system 10 can include the tracking system 44, the DRF 54, the DRF tracker 54*a*, a navigation control module 200 and the display 36. Each of the DRF 54 and the DRF tracker 54*a* can include the tracking device 58. The tracking system 44 can comprise an electromagnetic tracking system 44 or an optical tracking system 44*b*, and will generally be referred to as the tracking system 44. The tracking system 44 can receive start-up data 202 from the navigation control module 200. Based on the start-up data 202, the tracking system 44 can set activation signal data 204 that can activate the coil arrays 46, 47 to generate an electromagnetic field to which the tracking devices 58 in the DRF 54 and DRF tracker 54*a* can respond. The tracking system 44 can also set tracking data 208 to the navigation control module 200, as will be discussed. The tracking data 208 can include data regarding the coordinate locations (positions and orientations) of the DRF 54 and DRF tracker 54*a*, which can include a difference existing between the coordinate location (position and orientation) of the DRF 54 and the coordinate location (position and orientation) of the DRF tracker 54*a* in the navigation field due to movement of either the DRF 54 and/or DRF tracker 54*a* as computed from the sensor data 210.

When the tracking devices 58 are activated, the tracking devices 58 can transmit sensor data 210 indicative of a location of the tracking device 58 in the patient space to the tracking system 44. Based on the sensor data 210 received by the tracking system 44, the tracking system 44 can generate and set the tracking data 208 for the navigation control module 200.

The navigation control module 200 can receive the tracking data 208 from the tracking system 44 as input. The navigation control module 200 can also receive patient image data 100 as input. The patient image data 100 can comprise images of the anatomy of the patient 12 obtained from a pre- or intra-operative imaging device, such as the images obtained by the imaging device 14. Based on the tracking data 208 and the patient image data 100, the navigation control module 200 can generate image data 102 for display on the display 36. The image data 102 can comprise the patient image data 100 superimposed with an icon 103 of the instrument 52, as shown in FIG. 1, and/or can comprise notification data 212 that the DRF 54 and/or DRF tracker 54*a* has moved relative to the patient 12 such that the registration is inaccurate. For example, the notification data 212 can comprise a pop-up message and/or symbol that indicates that the registration is no longer accurate and that the DRF 54 and/or DRF tracker 54*a* should be examined, and/or an audible tone or message regarding the same. The image data 102 could also comprise a graphical illustration of the DRF 54, DRF tracker 54*a*, point P, etc. as shown in FIGS. 8-11.

Figure 13:
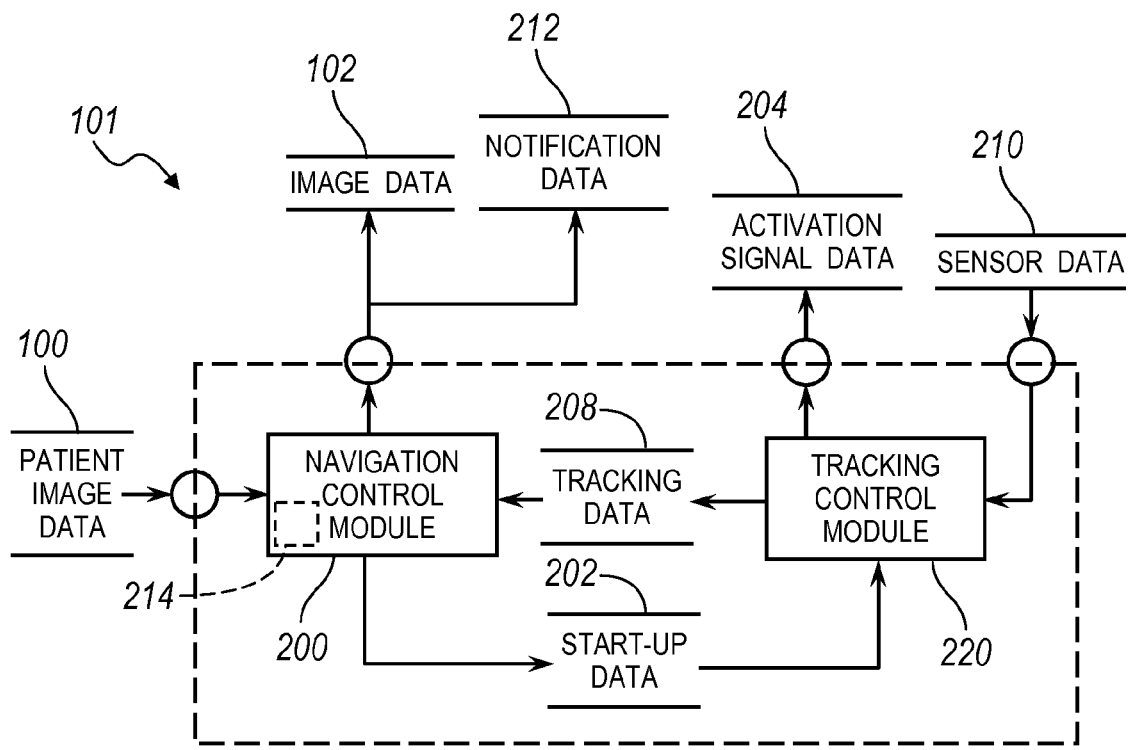
FIG. 13 is a dataflow diagram illustrating a control system performed by a control module associated with the navigation system of FIG. 1.

With reference now to FIG. 13, a dataflow diagram illustrates an exemplary control system that can be embedded within the control module 101. Various embodiments of the tracking control system according to the present disclosure can include any number of sub-modules embedded within the control module 101. The sub-modules shown may be combined and/or further partitioned to similarly determine the relative motion of the DRF 54 based on the signals generated by the tracking devices 58 of the DRF 54 and DRF tracker 54*a*. In various embodiments, the control module 101 includes the tracking system 44 that can implement a tracking control module 220, and the workstation 34 that can implement the navigation control module 200. It should be noted that the tracking control module 220 can be implemented by the tracking system 44 and the navigation control module 200 can be implemented on the workstation 34, however, both of the tracking control module 220 and the navigation control module 200 could be implemented on the workstation 34, if desired.

The tracking control module 220 can receive as input the start-up data 202 from the navigation control module 200 and sensor data 210 from the tracking device 58. Upon receipt of the start-up data 202, the tracking control module 220 can output the activation signal data 204 for the tracking devices 58. Upon receipt of the sensor data 210, the tracking control module 220 can set the tracking data 208 for the navigation control module 200. As discussed, the tracking data 208 can include data regarding the coordinate locations (positions and orientations) of the DRF 54 and DRF tracker 54*a*, which can include the difference existing between the coordinate locations of the DRF 54 and the DRF tracker 54*a*.

The navigation control module 200 can receive as input the tracking data 208 and patient image data 100. Based on the tracking data 208, the navigation control module 200 can determine the appropriate patient image data 100 and/or notification data 212 for display on the display 36, and can output both the tracking data 208 and the patient image data 100 as image data 102. Optionally, the navigation control module 200 can include a data store 214. The data store 214 can enable the navigation control module 200 to store and retrieve the tracking data 208 received from the tracking control module 220. Thus, the navigation control module 200 can query the data store 214 for the last received coordinate locations (positions and orientations) of the DRF 54 and DRF tracker 54*a* and/or last known relative difference existing between the coordinate locations of the DRF 54 and DRF tracker 54*a*, and based on the last known coordinate locations, the navigation control module 200 can determine if the DRF 54 and/or DRF tracker 54*a* have moved relative to the patient 12 based on a change in the last known difference between the coordinate locations of the DRF 54 and DRF tracker 54*a* and the current difference existing between the coordinate locations of the DRF 54 and DRF tracker 54*a*. Further, the navigation control module 200 can determine, based on the stored tracking data 208, whether a change in the difference between the coordinate locations of the DRF 54 and DRF tracker 54*a* is cyclic due to the patient 12 undergoing respiration.

Figure 14:
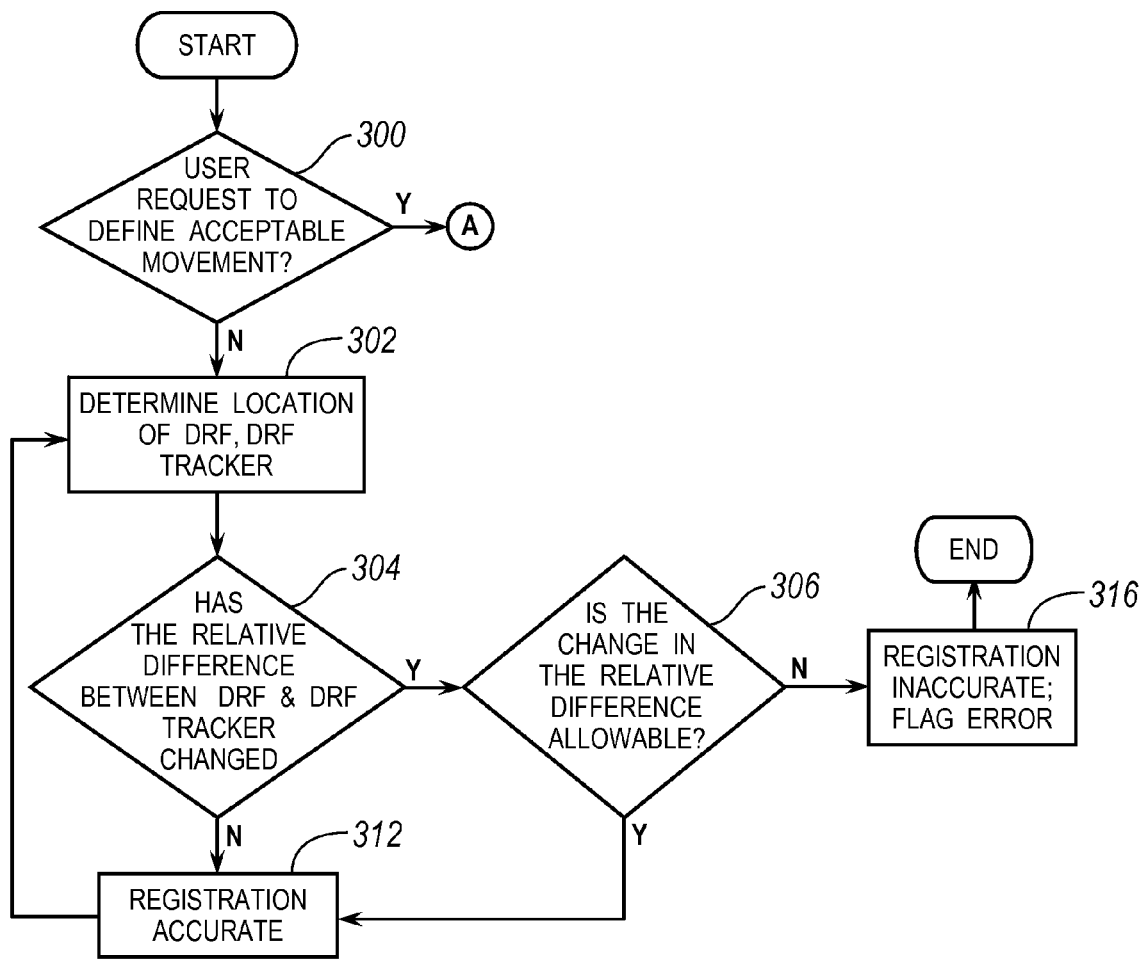
FIG. 14 is a flowchart illustrating a control method performed by the control module.

With reference now to FIG. 14, a flowchart diagram illustrates an exemplary method performed by the control module 101. At decision block 300, the method can decide if a user has requested, via the user input device 38, to define an acceptable boundary volume for the movement of the DRF 54 and/or the DRF tracker 54*a* relative to the anatomical structure of the patient 12 (FIGS. 8-11). If the user wishes to define an acceptable boundary volume M for the movement of the DRF 54 and/or DRF tracker 54*a*, then the method goes to A on FIG. 15. Otherwise, at block 302, the method can determine the coordinate locations (positions and orientations) of the DRF 54 and the DRF tracker 54*a* in the patient space or navigation field (FIGS. 1-2). The location of the DRF 54 and DRF tracker 54*a* can comprise the sensor data 210 received by the tracking system 44 from the tracking device 58 of each of the DRF 54 and DRF tracker 54*a*.

At decision block 304, the method can determine if the difference existing between the coordinate locations of the DRF 54 and DRF tracker 54*a* has changed based on the last known difference between the DRF 54 and DRF tracker 54*a*. As discussed, the relative difference between the coordinate locations of the DRF 54 and DRF tracker 54*a* can be computed based on the known coordinate locations (positions and orientations) of the DRF 54 and the DRF tracker 54a. If the method determines that the difference between the coordinate locations has changed, then the method can go to decision block 306. Otherwise, the method can go to block 312. At block 312, the method can determine that registration is accurate. After the method determines that registration is accurate, the method can loop to block 302.

At decision block 306, the method can determine if a change in the difference existing between the coordinate locations of the DRF 54 and DRF tracker 54a is allowable. In this regard, for example, the method can determine if the length L and angle A of the vector $v_3$ has remained the same even with the change in the coordinate locations of the DRF 54 and DRF tracker 54a (FIGS. 3-4). The length L and angle A of the vector $v_3$ would remain the same in instances where the patient 12 has rotated or translated in the patient space. If the relative difference between the coordinate locations of the DRF 54 and DRF tracker 54a has not changed, for example, if the length L and angle A of the vector $v_3$ has not changed, then the method goes to block 312.

Otherwise, if the difference between the coordinate locations has changed due to the movement of the DRF 54 and/or DRF tracker 54a, then the method can go to block 316. At block 316, the method can determine that registration is inaccurate and the method can flag an error to notify the user that registration is inaccurate, such as by displaying the notification data 216 on the display 36. Then, the method can end.

Figure 15:
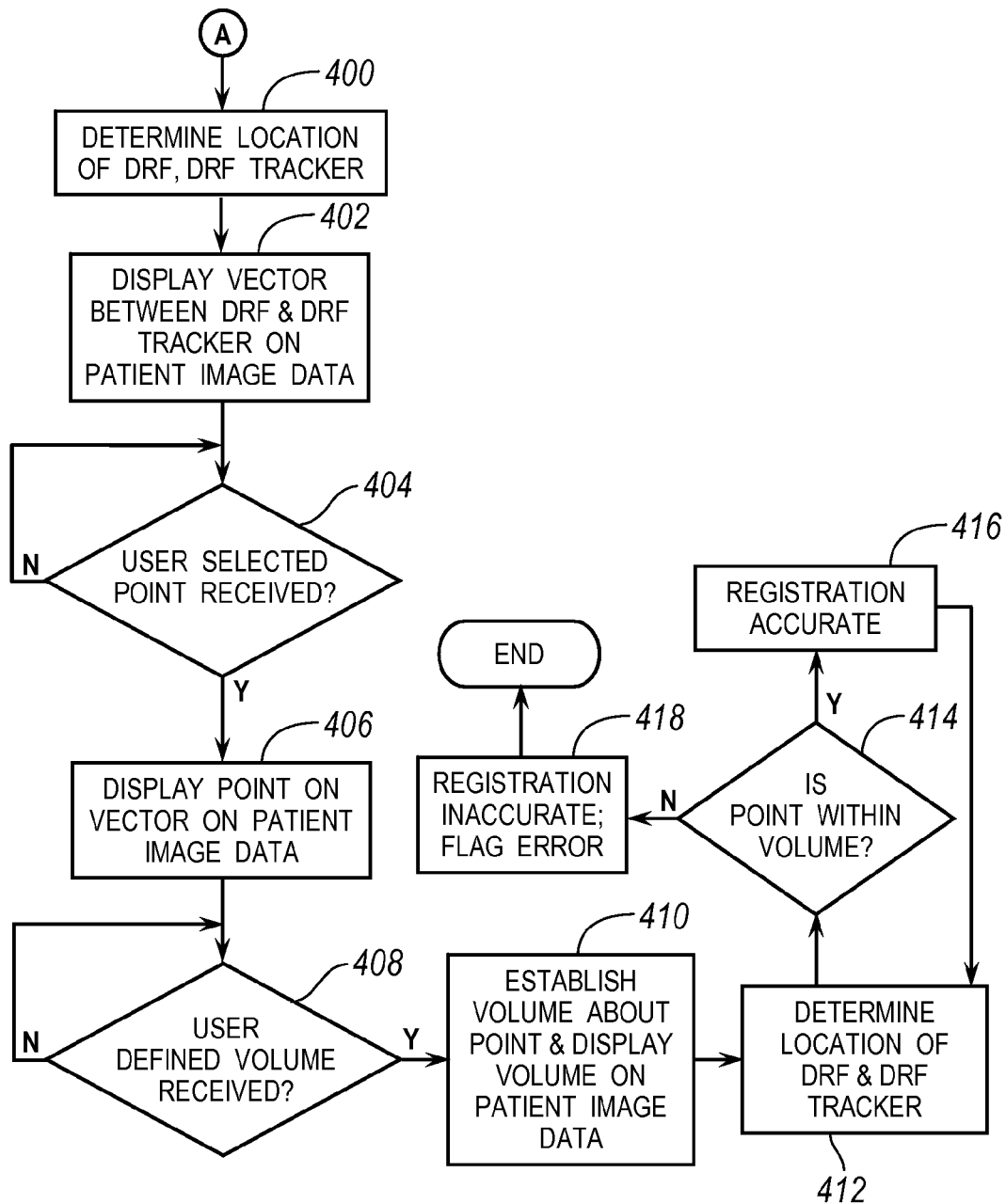
FIG. 15 is a flowchart illustrating the control method performed by the control module.

With reference to FIG. 15, at block 400 the method can determine the coordinate locations (positions and orientations) of the DRF 54 and the DRF tracker 54a in the patient space. At block 402, the method can display the DRF 54 and the DRF tracker 54a with the vector $v_3$ drawn between the DRF 54 and DRF tracker 54a on the display 36 (FIG. 8). The DRF 54, DRF tracker 54a and the vector $v_3$ can be displayed on the patient image data 100. At decision block 404, the method can determine if the user has selected a desired point P on the vector $V_3$ (FIG. 9). The user may select the desired point P through any appropriate user input device 38. The method can loop until a user input is received.

After the user has selected a desired point P on the vector $v_3$, at block 406, the method can display the desired point P on the vector $v_3$ with the patient image data 100 on the display 36. Then, at decision block 408, the method can determine if the user has defined a boundary volume M for the movement of the DRF 54 relative to the anatomical structure of the patient 12.

Once the user has defined the boundary volume M, at block 410, the method can establish the boundary volume M about the desired point P, which can be displayed about the vector $v_3$ on the patient image data 100 (FIG. 10). Then, at block 412, the method can determine the coordinate locations (positions and orientations) of the DRF 54 and the DRF tracker 54a in the patient space. At decision block 414, the method can determine if the desired point P is within the boundary volume M when the vector $v_3$ is drawn between the DRF 54 and DRF tracker 54a at their current coordinate locations (positions and orientations) (FIG. 11). If the desired point P is within the boundary volume M, then the method can go to block 416. At block 416, the method can determine that registration is accurate, and then the method can loop to block 412.

Otherwise, if the desired point P is not within the boundary volume M, then the method can go to block 418. At block 418, the method can determine that registration is inaccurate, and can notify the user that the registration is inaccurate. Then, the method can end.

Therefore, the navigation system 10 of the present disclosure can maintain registration accuracy throughout the surgical procedure. In this regard, the use of the DRF 54 and the DRF tracker 54a with the coil arrays 46, 47 can maintain registration accuracy by identifying unplanned motion of the DRF 54 and/or DRF tracker 54a in the navigation field relative to the anatomical structure of the patient 12 during the surgical procedure. By tracking the location of the DRF 54 relative to the anatomical structure of the patient 12 with the DRF tracker 54a, the navigation system 10 can ensure more accurate patient image data 100 is output on the display 36. Further, the tracking of the DRF 54 with the DRF tracker 54a can allow the navigation system 10 to notify the operator 39 if the DRF 54 and/or DRF tracker 54a moves relative to the anatomical structure of the patient 12 in the navigation field. This can alert the operator 39 to verify the position of the DRF 54 and/or DRF tracker 54a in the patient space before proceeding further with the surgical procedure.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. A system for tracking a patient comprising:
a display;
a first reference frame adapted to be coupled to a first portion of an anatomical structure;
a second reference frame adapted to be coupled to a second portion of the anatomical structure, the second reference frame positioned substantially vertically opposite the first reference frame during the tracking of the patient;
a first tracking device coupled to the first reference frame;
a second tracking device coupled to the second reference frame;
a tracking system configured to track respective positions of the first tracking device and the second tracking device to ensure that a position of the first reference frame relative to the anatomical structure is substantially the same during a surgical procedure, and
a navigation system configured to determine respective positions of the first reference frame and the second reference frame during the surgical procedure based on the respective tracked positions of the first tracking device and the second tracking device,
wherein the navigation system determines if the position of the first reference frame has changed more than a predetermined amount relative to the first portion of the anatomical structure by determining a change in a difference in relative location of the first reference frame and the location of the second reference frame during the surgical procedure, and wherein the navigation system determines that the difference has changed if a location of a user-defined point on a vector drawn between the respective positions of the first reference frame and the second reference frame superimposed on a displayed image of the anatomical structure on the display is outside of a user-selected boundary volume defined on the image.

2. The system of claim 1, further comprising:
an imaging device that is operable to acquire the image of the anatomical structure.

3. The system of claim 2, further comprising:
an instrument that includes a third tracking device,
wherein the tracking system tracks the third tracking device of the instrument and the navigation system determines a position of the instrument relative to the anatomical structure based on the tracking of the third tracking device.

4. The system of claim 3, further comprising:
a display that displays the image of the anatomical structure with at least one of the first reference frame, the second reference frame, the instrument and combinations thereof superimposed on the image at a location that corresponds to the position of the first reference frame, the second reference frame, and the instrument relative to the anatomical structure.

5. The system of claim 4, wherein the display further displays notification data that indicates if the position of the first reference frame has changed relative to the anatomical structure during the surgical procedure.

6. The system of claim 3, wherein the first tracking device and the second tracking device comprises at least one optical tracking device to track at least one degree of freedom information.

7. The system of claim 3, wherein the first tracking device and the second tracking device comprises at least one electromagnetic tracking device selected from the group comprising: an electromagnetic receiver tracking device, an electromagnetic transmitter tracking device and combinations thereof.

8. The system of claim 1, wherein the navigation system determines whether the location of the first reference frame or the location of the second reference frame has changed during the surgical procedure, and automatically updates tracking data associated with the changed one of the first reference frame and the second reference frame to account for the changed location of the first reference or second reference frame.

9. The system of claim 8, wherein the display further displays notification data that indicates that the tracking data has been updated to account for a new location of either the first reference frame or the second reference frame.

10. The system of claim 1, wherein the navigation system determines that the difference has changed if a length, an angle or combination thereof of the vector drawn between the first reference frame and the second reference frame has changed and the location of one of the first reference frame and the second reference frame has changed and the change in the length, angle or combination thereof does not fall in a cyclical pattern.

11. The system of claim 1, wherein the first reference frame is configured to be coupled to the first portion of the anatomical structure adjacent to an area of interest.

12. The system of claim 11, wherein the area of interest is selected from the group comprising a patient, a surgical site, an anatomical site, a navigation area and combinations thereof.

13. The system of claim 1, further comprising a user input device configured to input the user-defined point.

14. A system for tracking a patient comprising:
a display;
a first reference frame adapted to be coupled to a first portion of an anatomical structure;
a second reference frame adapted to be coupled to a second portion of the anatomical structure, the second reference frame positioned substantially vertically opposite the first reference frame during the tracking of the patient;
a first tracking device coupled to the first reference frame;
a second tracking device coupled to the second reference frame;
a tracking system configured to track a position of first tracking device and the second tracking device to ensure that the position of the first reference frame relative to the anatomical structure is substantially the same during a surgical procedure, and
a navigation system configured to determine respective positions of the first reference frame and the second reference frame during the surgical procedure based on the respective tracked positions of the first tracking device and the second tracking device,
wherein the navigation system determines if the position of the first reference frame has changed more than a predetermined amount relative to the first portion of the anatomical structure by determining a change in a difference in relative location of the first reference frame and the location of the second reference frame during the surgical procedure, and
wherein the navigation system determines that the difference has changed if a length, an angle or combination thereof of a vector drawn between the first reference frame and the second reference frame superimposed on a displayed image of the anatomical structure on the display has changed and the positions of both of the first reference frame and the second reference frame have changed.

15. A method for tracking a patient comprising:
coupling a first reference frame to a first portion of an outer surface defined by an anatomical structure, the first reference frame including a first tracking device;
coupling a second reference frame to a second portion of the outer surface defined by the anatomical structure opposite the first reference frame such that a normal vector from the second reference frame extends substantially towards the first reference frame during the tracking of the patient, the second reference frame including a second tracking device;
tracking a position of the first tracking device of the first reference frame and the second tracking device of the second reference frame; and
determining if the first reference frame has moved more than a predetermined amount relative to the first portion of the anatomical structure by:
determining a location of the first reference frame and the second reference frame based on the tracking of the first reference frame and the second reference frame;
drawing a vector between superimposed determined locations of the first reference frame and the second reference frame on a displayed image on a display; and determining if a difference between the location of the first reference frame and the location of the second reference frame has changed during the surgical procedure based upon the vector defined in the image.

16. The method of claim 15, further comprising:
displaying a position of at least one of the first reference frame, the second reference frame, or combinations thereof relative to the anatomical structure on the display.

17. The method of claim 15, further comprising:
displaying notification data that indicates if the position of the first reference frame has changed relative to the anatomical structure during the surgical procedure on the display.

18. The method of claim 15, wherein determining if the first reference frame has moved relative to the anatomical structure further comprises:
determining that the difference has changed if a user-defined point on the vector is outside of a user-selected boundary volume.

19. The method of claim 15, wherein determining if the first reference frame has moved relative to the anatomical structure further comprises:
determining that the difference has changed if a length, an angle or combination thereof of the vector has changed and the locations of both of the first reference frame and the second reference frame have changed.

20. The method of claim 15, further comprising:
determining if the location of the first reference frame or the second reference frame has changed; and
automatically updating the tracking of the first reference frame or second reference frame to compensate for the new location of the first reference frame or second reference frame.

21. The method of claim 20, further comprising:
notifying the operator that the tracking of the first reference frame or second reference frame has changed based on the new location of the first reference frame or second reference frame.

22. The method of claim 15, wherein determining if the first reference frame has moved relative to the anatomical structure further comprises:
determining that the difference has changed if a length, an angle or combination thereof of the vector has changed, the location of one of the first reference frame and the second reference frame has changed and the change in the length, angle, position or combination thereof does not fall in a cyclical pattern.

23. The method of claim 15, further comprising:
adhesively coupling at least one of the first reference frame to the first portion of the anatomical structure, the second reference frame to the second portion of the anatomical structure, or combinations thereof.

24. The method of claim 23, wherein the first reference frame and the second reference frames are adapted to be positioned generally opposite one another on a thoracic region of a patient, and the tracking of the first reference frame and second reference frame determines the respiratory motion, respiratory rate or combinations thereof, associated with the patient.

25. A system for tracking a patient comprising:
a first reference frame adapted to be coupled to a first portion of an outer surface defined by an anatomical structure of the patient;
a second reference frame adapted to be coupled to a second portion of the outer surface defined by the anatomical structure, the second reference frame coupled substantially opposite the first reference frame such that the first reference frame and the second reference frame are positioned at opposite ends of a transverse plane defined through the outer surface during the tracking of the patient;
a first tracking device coupled to the first reference frame;
a second tracking device coupled to the second reference frame;
a tracking system configured to track respective locations of the first tracking device and the second tracking device;
a navigation system configured to determine respective locations of the first reference frame and the second reference frame based on the tracking of the first tracking device and the second tracking device; and
a display that displays an image of the anatomical structure,
wherein the navigation system determines if the image displayed is accurate by determining if a difference existing between the location of the first reference frame and the location of the second reference frame changes more than a predetermined amount,
wherein the navigation system determines that the difference has changed if a length, an angle or combination thereof of a vector drawn between the respective locations of the first reference frame and the second reference frame has changed, the location of one of the first reference frame and the second reference frame superimposed on the displayed image has changed and the change in the length, angle or combination thereof does not fall in a cyclical pattern.

26. The system of claim 25, further comprising:
an instrument; and
a third tracking device coupled to the instrument to enable the tracking system to track the third tracking device,
wherein the navigation system determines a position of the instrument relative to the anatomical structure based on the tracking of the third tracking device and the display displays the image of the anatomical structure with at least one of the first reference frame, the second reference frame, the instrument and combinations thereof superimposed on the image at a location that corresponds to the position of the first reference frame, the second reference frame, and the instrument relative to the anatomical structure.

27. The system of claim 25, wherein the navigation system determines navigation is inaccurate if the difference between the location of the first reference frame and the second reference frame has changed during the surgical procedure.

28. The system of claim 25, wherein the location of the first reference frame and the second reference frame is defined by at least three degrees of freedom.

* * * * *